US011719482B2

(12) United States Patent
Buzzi et al.

(10) Patent No.: US 11,719,482 B2
(45) Date of Patent: *Aug. 8, 2023

(54) AIR FILTRATION SYSTEM FOR ANTIMICROBIAL REFRIGERATORS

(71) Applicant: WHIRLPOOL CORPORATION, Benton Harbor, MI (US)

(72) Inventors: Ermanno Buzzi, Varese (IT); Gabriele Candiani, Milan (IT); Alberto Cigada, Milan (IT); Fabio Andrea Cigada, Milan (IT); Luigi De Nardo, Milan (IT); Muhammad Khizar, St. Joseph, MI (US); Maria Paola Pirovano, Molteno (IT)

(73) Assignee: Whirlpool Corporation, Benton Harbor, MI (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/334,197

(22) Filed: May 28, 2021

(65) Prior Publication Data

US 2021/0285713 A1 Sep. 16, 2021

Related U.S. Application Data

(63) Continuation of application No. 16/115,836, filed on Aug. 29, 2018, now Pat. No. 11,022,361.

(51) Int. Cl.
*F25D 17/04* (2006.01)
*F25D 17/06* (2006.01)

(52) U.S. Cl.
CPC ......... *F25D 17/042* (2013.01); *F25D 17/065* (2013.01); *F25D 2317/041* (2013.01);
(Continued)

(58) Field of Classification Search
CPC ................ F25D 17/042; F25D 17/065; F25D 2317/041; F25D 2317/0415; F25D 2317/0417
See application file for complete search history.

(56) References Cited

U.S. PATENT DOCUMENTS 4,909,040 A 3/1990 Fletrin
5,919,422 A 7/1999 Yamanaka et al.
(Continued)

FOREIGN PATENT DOCUMENTS

| | | | |
|---|---|---|---|
| CN | 103623452 | A | 3/2014 |
| EP | 2527769 | A2 | 11/2012 |
| JP | 2000279493 | A | 10/2000 |

OTHER PUBLICATIONS

Vilas Desai: "Antimicrobial Activity of Titanium Dioxide Nanoparticles Synthesized by Sol-Gel Technique—SciAlert Responsive Version", Jan. 1, 2009 (Jan. 1, 2009), XP055651227, Retrieved from the Internet: URL:https://scialart.net/fulltextmobile/?doi=jm.2009.97.103 [retrieved on Dec. 10, 2019].
(Continued)

*Primary Examiner* — Filip Zec
(74) *Attorney, Agent, or Firm* — Price Heneveld LLP

(57) ABSTRACT

A refrigerator includes a rear assembly panel coupled with an assembly cover panel that includes at least one vent. At least one circulation fan is positioned between the rear assembly panel and the assembly cover panel and is proximate the at least one vent. A filter is positioned between the rear assembly panel and the assembly cover panel and is coupled to a photocatalyst to form an activated carbon filter. A light-emitting diode (LED) panel assembly includes a plurality of LEDs positioned on the rear assembly panel and is positioned to project light on the activated carbon filter. An air circulation path extends through the at least one vent and the activated carbon filter and is configured to direct air
(Continued)

along the air circulation path, and the activated carbon filter is configured to filter airborne bacteria and particulate matter from the air as the air passes through the activated carbon filter.

20 Claims, 16 Drawing Sheets

(52) U.S. Cl.
CPC ................ *F25D 2317/0415* (2013.01); *F25D 2317/0417* (2013.01)

(56) References Cited

U.S. PATENT DOCUMENTS

| | | | | |
|---|---|---|---|---|
| 5,933,702 | A | 8/1999 | Goswami | |
| 6,238,631 | B1 | 5/2001 | Ogata et al. | |
| 6,606,869 | B2 | 8/2003 | Takahashi et al. | |
| 6,736,885 | B2 | 5/2004 | Kaiser | |
| 6,797,044 | B2 | 9/2004 | Ou Yang et al. | |
| 7,063,820 | B2 | 6/2006 | Goswami | |
| 7,704,913 | B2 | 4/2010 | Tani et al. | |
| 9,803,909 | B2 | 10/2017 | Son et al. | |
| 9,803,910 | B2 | 10/2017 | Kim et al. | |
| 9,903,634 | B2 | 2/2018 | Son et al. | |
| 10,712,084 | B2 | 7/2020 | Choi et al. | |
| 2003/0024254 | A1 | 2/2003 | Yoshida et al. | |
| 2005/0084717 | A1 | 4/2005 | Tani et al. | |
| 2005/0268623 | A1 | 12/2005 | Urakubo et al. | |
| 2007/0193875 | A1 | 8/2007 | Ham et al. | |
| 2007/0266725 | A1 | 11/2007 | Anikhindi et al. | |
| 2008/0274018 | A1 | 11/2008 | Kawai et al. | |
| 2008/0286643 | A1 | 11/2008 | Iwasaki | |
| 2009/0098014 | A1 | 4/2009 | Longstaff | |
| 2009/0123343 | A1 | 5/2009 | Kwiatkowski | |
| 2009/0136389 | A1 | 5/2009 | Park | |
| 2009/0162567 | A1 | 6/2009 | Tseng et al. | |
| 2010/0024462 | A1 | 2/2010 | Kamisako et al. | |
| 2012/0025104 | A1* | 2/2012 | Park | F25D 17/042 250/492.1 |
| 2013/0104579 | A1 | 5/2013 | Zhou | |
| 2014/0360213 | A1 | 12/2014 | Son et al. | |
| 2015/0033784 | A1 | 2/2015 | Park et al. | |
| 2015/0064069 | A1 | 3/2015 | Yi et al. | |
| 2015/0238644 | A1 | 8/2015 | Sung et al. | |
| 2016/0047587 | A1 | 2/2016 | Sasaki et al. | |
| 2016/0341467 | A1* | 11/2016 | Mitchell | F25D 17/042 |
| 2017/0246333 | A1 | 8/2017 | Carbone et al. | |
| 2017/0251682 | A1* | 9/2017 | Kamei | F25D 11/00 |
| 2017/0307280 | A1 | 10/2017 | Schmidt et al. | |
| 2018/0099062 | A1 | 4/2018 | Campalans et al. | |
| 2018/0238613 | A1 | 8/2018 | Choi et al. | |
| 2019/0128587 | A1* | 5/2019 | Murray | A61L 9/014 |
| 2020/0326115 | A1* | 10/2020 | Postgate | B65D 88/74 |

OTHER PUBLICATIONS

Abdel-Fatah Wafa I et al: "Role of silver nanoparticles in imparting antimicrobial activity of titanium dioxide", Materials Letters, Elsevier, Amsterdam, NL, vol. 179, May 9, 2016 (May 9, 2016, pp. 190-193, XP029562445, ISSN: 0167-577X, DOI: 10,1016/J.MATLET.2016.05.063.

Juliane Maria Guerreiro-Tanomaru et al.: "Effect of Zirconium Oxide and Zinc Oxide Nanopatricles on Physicochemical Properties and Antibifilm Activity of a Calcium Silicate-Based Material", The Scientific World Journal, vol. 2014, Jan. 1, 2014 (Jan. 1, 2014), pp. 1-6, XP055651394, ISSN: 2356-6140, DOI: 10,1155/2014/975213.

A. Cochis: "Data in support of Gallium (Ga3+) antibacterial activities to counteract *E. coli* and S. epidermidis biofilm formation onto pro-osteonintegrative titanium surfaces", Data in Brief., vol. 6, Jan. 22, 2016 (Jan. 22, 2016), pp. 758-762, XP055631750, DOI: 10.1016/j.dib.2016.01.024.

* cited by examiner

AIR FILTRATION SYSTEM FOR ANTIMICROBIAL REFRIGERATORS

CROSS-REFERENCE TO RELATED APPLICATION

This application is a continuation of U.S. application Ser. No. 16/115,836, filed on Aug. 29, 2018, now U.S. Pat. No. 11,022,361, entitled "AIR FILTRATION SYSTEM FOR ANTIMICROBIAL REFRIGERATORS," the disclosure of which is hereby incorporated herein by reference in its entirety.

FIELD OF THE INVENTION

The present device generally relates to an air filtration system for a refrigerator, and more specifically, to air purifying assemblies used in conjunction to filter microbes, volatile organic compounds, and particulate matter from a refrigerator.

BACKGROUND OF THE INVENTION

With the latest development of extra-large capacity refrigerators, there has been an emerging demand for highly robust antimicrobial technology such as air disinfection systems for food preservation and related features. Such systems are used to avoid the spoilage of food and produce stored in refrigerators for extended periods. Due to the unavailability of adequate antimicrobial technology, huge amounts of food, including produce, can go wasted even when stored in adequately low temperature refrigerators. Moreover, because of the increasing cost of commodities and food product costs, consumers are demanding efficient food storage technology for its longevity without compromise to its freshness.

One food preservation technique currently being used includes titanium dioxide ($TiO_2$) charged using a mercury lamp lighting system but due to the harmful effects of the mercury lamp integrated in this system, it could not meet the specifications or expectations for an antimicrobial application. In addition, the use of mercury in these types of UV lamp systems could be extremely dangerous due to health hazards and other handling issues associated with mercury. Other preservation and antimicrobial techniques being used include ozonizer systems that are directly integrated into the refrigerator. However, with time, significant decline in ozonizer performance is reported and their high cost makes these applications prohibitively expensive. Nano-misting techniques have also been studied but due to the harmful nature of the zinc and silver used in the applied nanoparticles; these materials also did not meet consumer market requirements.

Accordingly, the need for an efficient and affordable antimicrobial filtration system is required in the market place for consumers to better accommodate food safety and longer storage times for valuable foodstuffs.

SUMMARY OF THE DISCLOSURE

According to one aspect of the present disclosure, a refrigerator includes a rear assembly panel that is coupled with an assembly cover panel. The assembly cover panel includes at least one vent. At least one circulation fan is positioned between the rear assembly panel and the assembly cover panel and is proximate the at least one vent. A filter is positioned between the rear assembly panel and the assembly cover panel and is coupled to a photocatalyst to form an activated carbon filter. A light-emitting diode (LED) panel assembly includes a plurality of LEDs positioned on the rear assembly panel. The LED panel assembly is positioned to project light on the activated carbon filter. An air circulation path extends through the at least one vent and the activated carbon filter. The at least one circulation fan is configured to direct air along the air circulation path and the activated carbon filter is configured to filter airborne bacteria and particulate matter from the air as the air passes through the activated carbon filter.

According to another aspect of the present disclosure, a refrigerator includes a rear assembly panel that is coupled with an assembly cover panel. The assembly cover panel includes first and second distal portions positioned on opposing sides of a central portion. The first and second distal portions each include at least one intake and the central portion includes at least one exhaust. An ultraviolet (UV) light activated photocatalyst is coupled to at least one filter forming an activated filter. A light-emitting diode (LED) panel assembly includes a plurality of LEDs positioned on the rear assembly panel. An air circulation path is defined by the rear assembly panel and the assembly cover panel and extends from the at least one intake, through the activated filter, and out through the at least one exhaust. The activated filter is configured to filter airborne bacteria and particulate matter from air as the air passes through the activated filter and out through the at least one exhaust to circulate filtered air.

According to still another aspect of the present disclosure, an antibacterial fan assembly includes a rear assembly panel coupled with an interior wall of an appliance. An assembly cover panel is coupled with the rear assembly panel to form a housing. The assembly cover panel includes a central portion that extends between first and second distal portions. The first and second distal portions of the assembly cover panel each include an air intake and the central portion of the assembly cover panel includes an air exhaust. At least one circulation fan is positioned between the rear assembly panel and assembly cover panel. Each of the circulation fans is aligned with a corresponding one of the air intakes. An activated filter is positioned proximate, and in circulation with, the air exhaust and includes a photocatalyst and an activated carbon. The photocatalyst is a titanium oxide ($TiO_2$) doped sol gel film. At least one light-emitting diode (LED) is positioned to project light on the activated filter.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

Figure 1B:
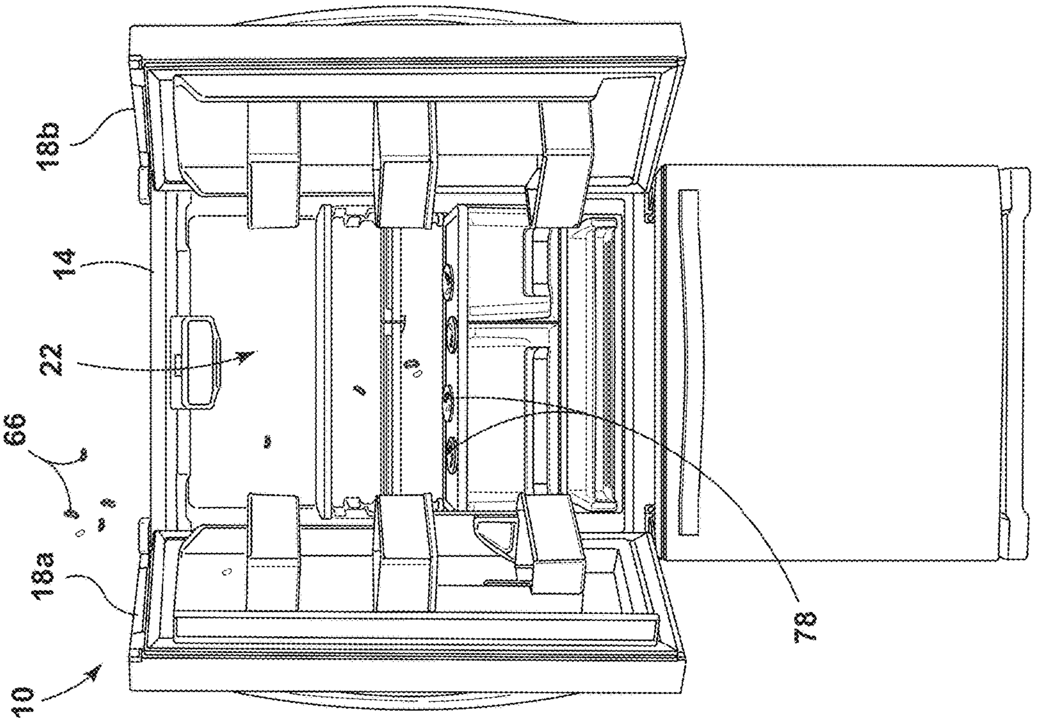
FIG. 1B is a front isometric view of a refrigerator having no food.
Figure 1A:
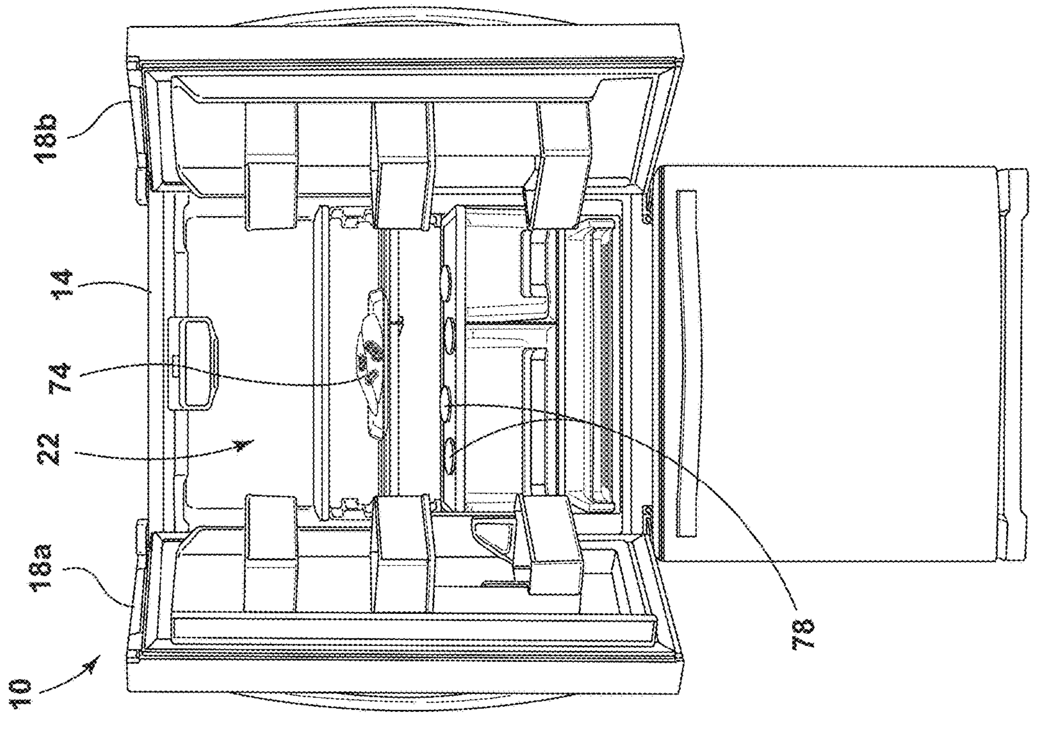
FIG. 1A is a front isometric view of a refrigerator having bacteria contaminated food.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Referring to FIGS. 1A-11B, the reference numeral 10 refers to a refrigerator. The refrigerator 10 includes a cabinet 14 coupled to one or more doors 18 forming a storage compartment 22. The refrigerator 10 additionally includes a first fan assembly 26 positioned on an interior surface 30 of a first cabinet wall 34, and a second fan assembly 38 positioned on the interior surface 30 of a second cabinet wall 42. The first and second fan assemblies 26, 38 each include: two or more circulation fans 46; a filter coupled to a photocatalyst 54 to form an activated filter 50; and a plurality of light emitting diodes (LEDs) 58 positioned to project light on the activated filter 50. An air circulation path 62 configured to direct air born bacteria 66 and particulate matter 70 within the storage compartment 22 contemporaneously into the first and second fan assemblies 26, 38 using the two or more circulation fans 46 and circulate filtered air into the storage compartment 22 through the activated filter 50 disposed in the air circulation path 62.

The first and second fan assemblies 26, 38 and/or the air purifying duct assembly 192 provide an antimicrobial technology for in-vitro time-dependent reduction of microbial populations after exposure to the activated filter 50 and corresponding UV and/or visible light LEDs 58. The technology incorporated into these fan assemblies 26, 38 includes the activated filter 50 and LEDs 58 providing an efficient air treatment capability that may interact with the deoxyribonucleic acid (DNA) and/or trigger a cascade of other biological reactions in harmful bacteria responsible for the spoilage of food stored at low temperatures in refrigerators. The disclosure herein provides a series of experiments performed according to the ASTM E 2315 and ISO 22196 international standards using minor modifications. In some aspects, the activated filter 50 includes the photocatalyst 54 made up of a photocatalytic nanostructured titanium dioxide ($TiO_2$) film, coating, or membrane deposited using sol-gel. The sol-gel is doped to impart the titanium dioxide ($TiO_2$) as the photocatalyst 54 that may be activated using visible light and/or an ultraviolet wavelength less than 833 nanometers (e.g., 280-700 nanometer wavelengths) using a 12 volt UV LED strip or panel (see FIG. 5B) is provided. In some aspects, the activated filter 50 and corresponding photocatalyst 54 may be activated using an ultraviolet wavelength less than about 400 nm and/or visible light ranging from about 390 nm to about 700 nm.

Referring now to FIGS. 1A-1D, a variety of different refrigerator environments were studied to determine how bacteria and other particulate matter may be introduced into the storage compartment 22 of the refrigerator 10. Each of the refrigerators 10 is shown having the cabinet 14 with the storage compartment 22 enclosed by the cabinet 14 and a first and second door **18*a*, 18*b*. In the first test environment illustrated in FIG. 1A, the introduction of bacterial contamination to the storage compartment 22 was accomplished by positioning a contaminated chicken breast 74 containing many different types of bacteria. The test environment provided in FIG. 1A demonstrated that the bacteria growing on the contaminated chicken breast 74 did not spread to or reach any of plurality of petri dishes 78** proving that refrigerator bacterial contamination is likely not due to food cross-contamination, except for direct food contact.

In the second test environment illustrated in FIG. 1B, the introduction of bacterial contamination to the storage compartment 22 was accomplished by circulating air from outside the refrigerator 10 by opening and closing the first and second refrigerator doors **18*a*, 18*b*. By opening and closing the refrigerator doors 18***a*, 18*b*, airborne bacteria 66 was introduced to the storage compartment 22 and was able to contact and grow in the petri dishes 78. The refrigerator 10 in FIG. 1B did not include any air filtration or circulation system. The test environment provided in FIG. 1B demonstrates that bacteria introduced into the refrigerator 10 and corresponding foodstuffs is likely determined by the introduction of airborne bacteria 66 during refrigerator door 18 opening and closing.

Figure 1D:
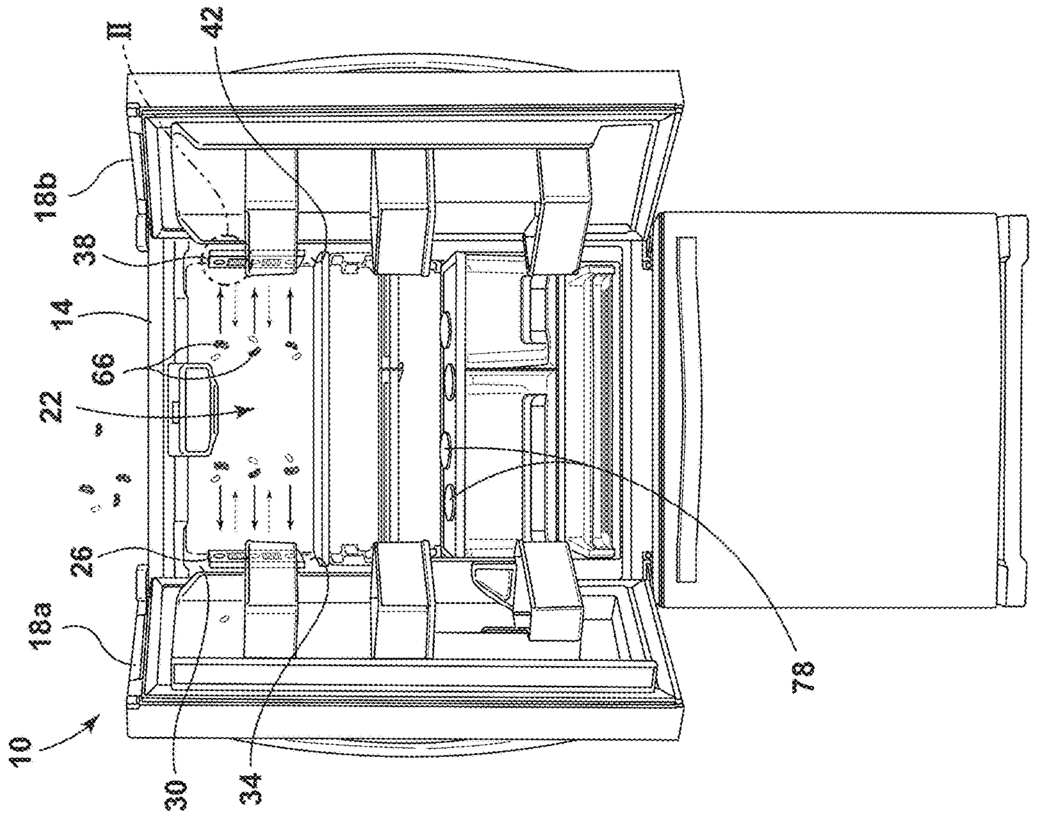
FIG. 1D is a front isometric view of a refrigerator having a first fan assembly and a second fan assembly according to some aspects of the disclosure.
Figure 1C:
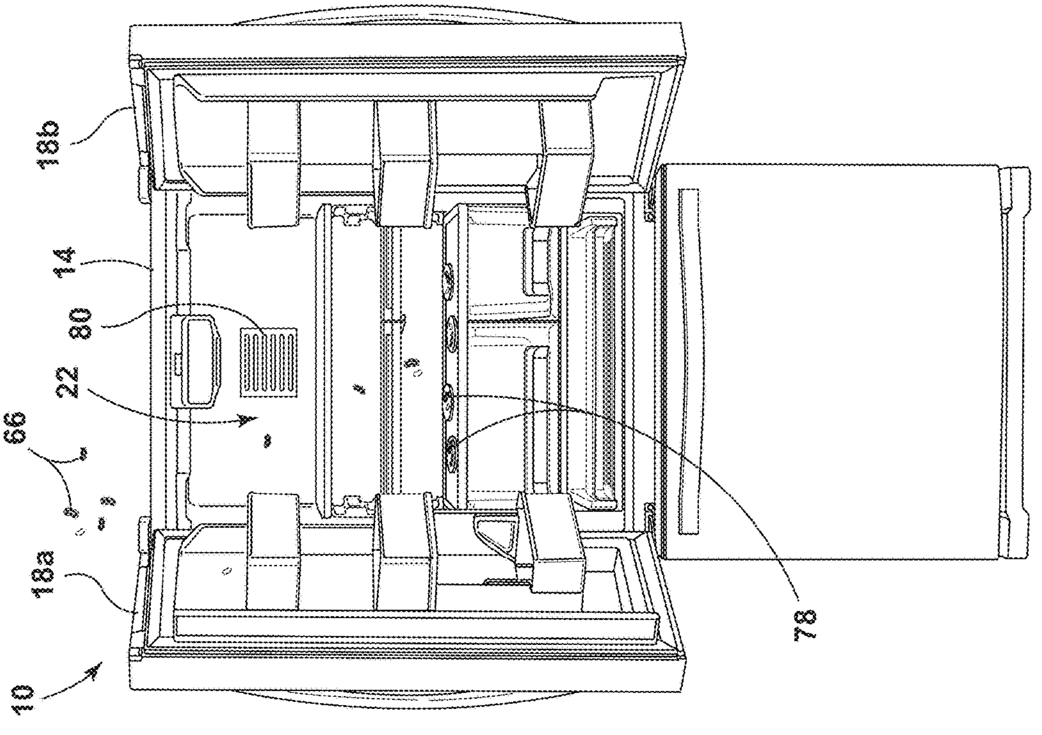
FIG. 1C is a front isometric view of a refrigerator having a standard circulation fan.

In the third test environment illustrated in FIG. 1C, the introduction of bacterial contamination to the storage compartment 22 was accomplished as described in FIG. 1B, by opening and closing the refrigerator doors 18*a*, 18*b*. The additional variable introduced in FIG. 1C includes a standard air filtration system 80 using only a single fan assembly which is currently implemented in many refrigerators. The test environment provided in FIG. 1C demonstrated that the single fan assembly air filtration system had minimal to no noticeable effect on the airborne bacteria 66 introduced into the storage compartment 22 of the refrigerator 10.

In the fourth test environment illustrated in FIG. 1D, the introduction of bacterial contamination to the storage compartment 22 was accomplished as described in FIGS. 1B and 1C, by opening and closing the refrigerator doors 18*a*, 18*b*. The refrigerator 10 in FIG. 1D additionally includes first and second fan assemblies 26, 38, each assembly equipped with circulation fans 46 and at least one activated filter 50 (see FIG. 2) initiated by at least one UV LED 58 (see FIG. 5B). The test environment provided in FIG. 1D demonstrated that the combination of two fan assemblies 26, 38 using UV activated filters 50 are able to reduce bacterial contamination in the storage compartment 22 by up to 70% more when compared to the environments provided in FIGS. 1B and 1C.

Figure 2:
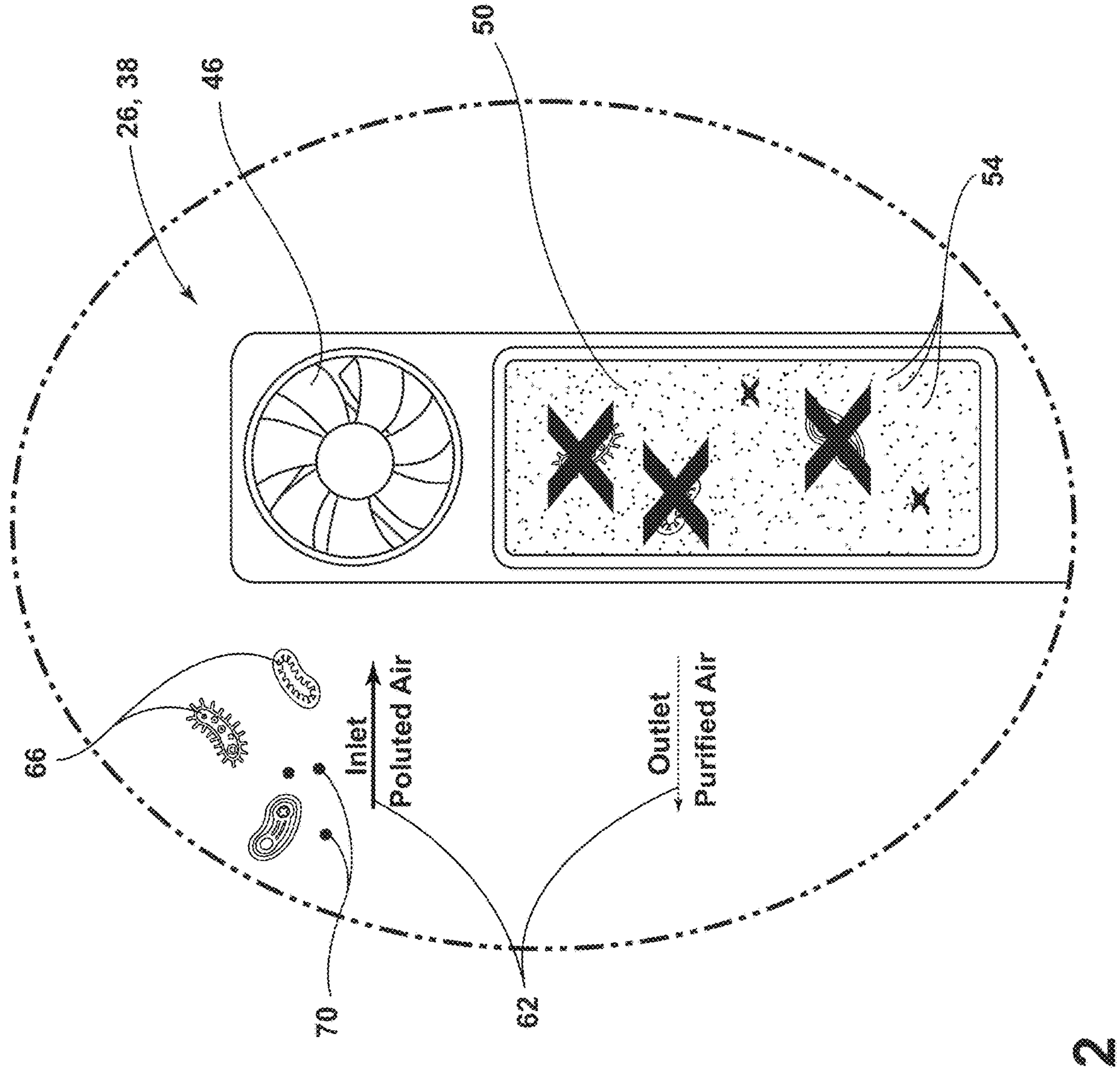
FIG. 2 is a partially schematic fragmentary view of the fan assembly taken at location II in FIG. 1D.

Referring now to FIG. 2, a partially schematic fragmentary view of the fan assembly 26, 38 is taken from the position marked II in FIG. 1D. As shown, airborne bacteria 66 and/or particulate matter 70 scattered throughout the storage compartment 22 are directed along the air circulation path 62 into one of the two fan assemblies 26, 38. The air circulation path 62 generally flows between the area of the storage assembly 22 and the two fan assemblies 26, 38 using two or more circulation fans 46 in each fan assembly 26, 38. As provided in FIGS. 1B, 1C, and 1D, the air introduced into the storage compartment 22 when opening the refrigerator doors 18*a*, 18*b* can include airborne bacteria 66 and/or particulate matter 70. Once the refrigerator doors 18*a*, 18*b* and corresponding storage compartment 22 are closed, the air circulation path 62 formed by the fan assemblies 26, 38 directs the airborne bacteria 66 and/or particulate matter 70 in through the circulation fans 46 and out through the activated filter 50 coupled to the photocatalyst 54. As the airborne bacteria 66 and/or particulate matter 70 contact the activated filter 50, one or more LEDs 58 (see FIG. 5B) can project UV and/or visible light onto the photocatalysts 54 of the activated filter 50. The photocatalyst 54 is activated by the UV light, which can then kill and/or damage the airborne bacteria 66. The particulate matter 70 can additionally be removed by the activated filter 50. The corresponding or resultant filtered air continues along the air circulation path 62 out through the filter 50 and back into the storage compartment 22 of the cabinet 14. In some aspects, a controller (not shown) drives the circulation fans 46 and LED's 58 (see FIG. 5B) as triggered by a pre-programmed schedule, the opening and closing of the refrigerator doors 18, the detection of odor, bacteria 66, and/or particulate matter 70 using, for example, a bio-sensor, and/or other triggers or factors known by one skilled in the art.

Figure 3:
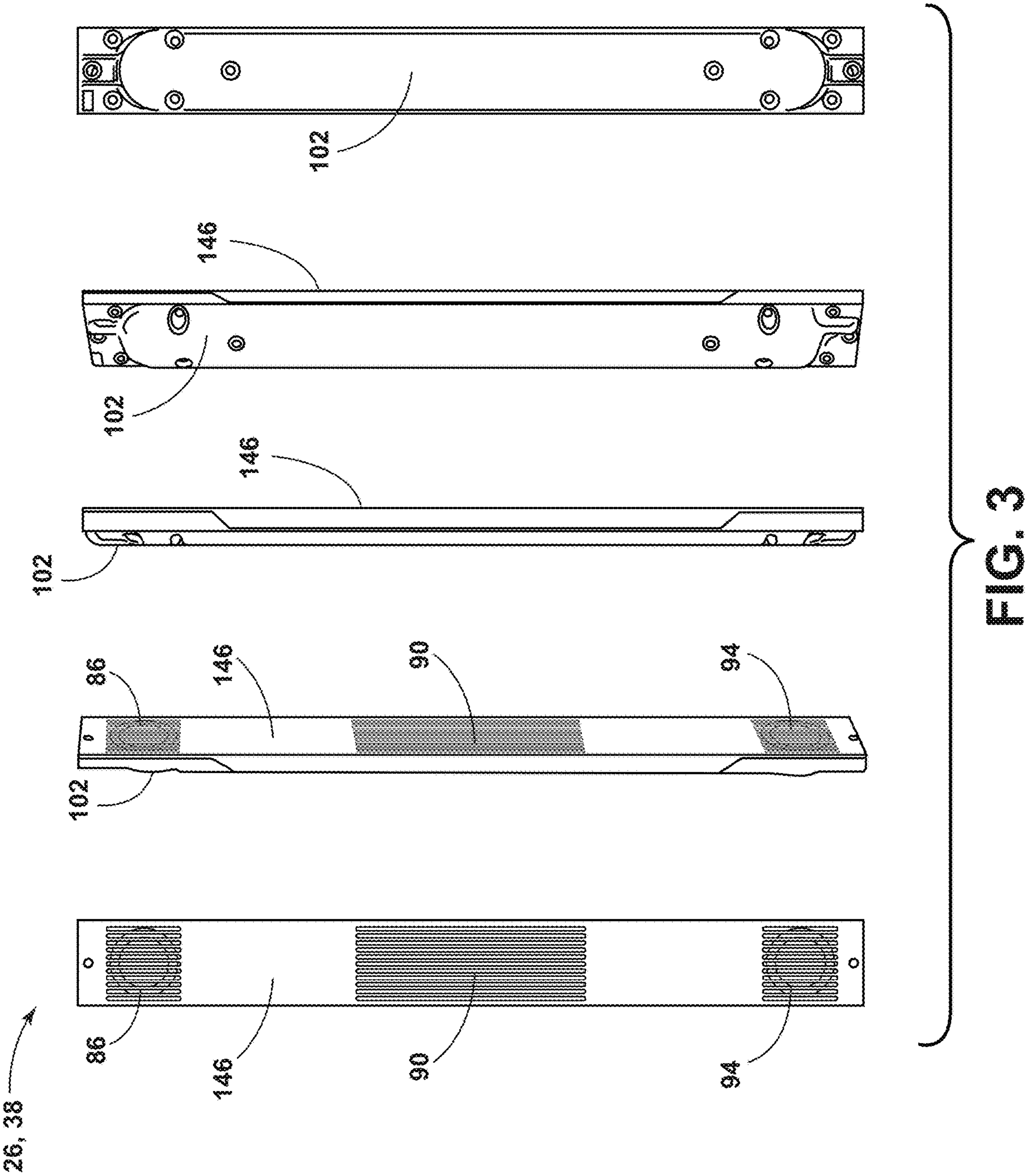
FIG. 3 is a rotating isometric view of a fan assembly according to some aspects of the present disclosure.

Referring now to FIG. 3, a rotating isometric view of the fan assemblies 26, 38 is provided. As shown, in some aspects, the fan assemblies 26, 38 include a first intake 86, an exhaust 90, and a second intake 94. The fan assemblies 26, 38 are rotated 180° to show the various structural features and shape of the device according to some aspects of the present disclosure. As illustrated, the fan assemblies 26, 38 each include a rear assembly panel 102 coupled to an assembly cover panel 146 that define the one or more intakes and exhausts in addition to the fixing members used to mount the internal hardware and the fan assemblies to the refrigerator 10, respectively.

Figure 4B:
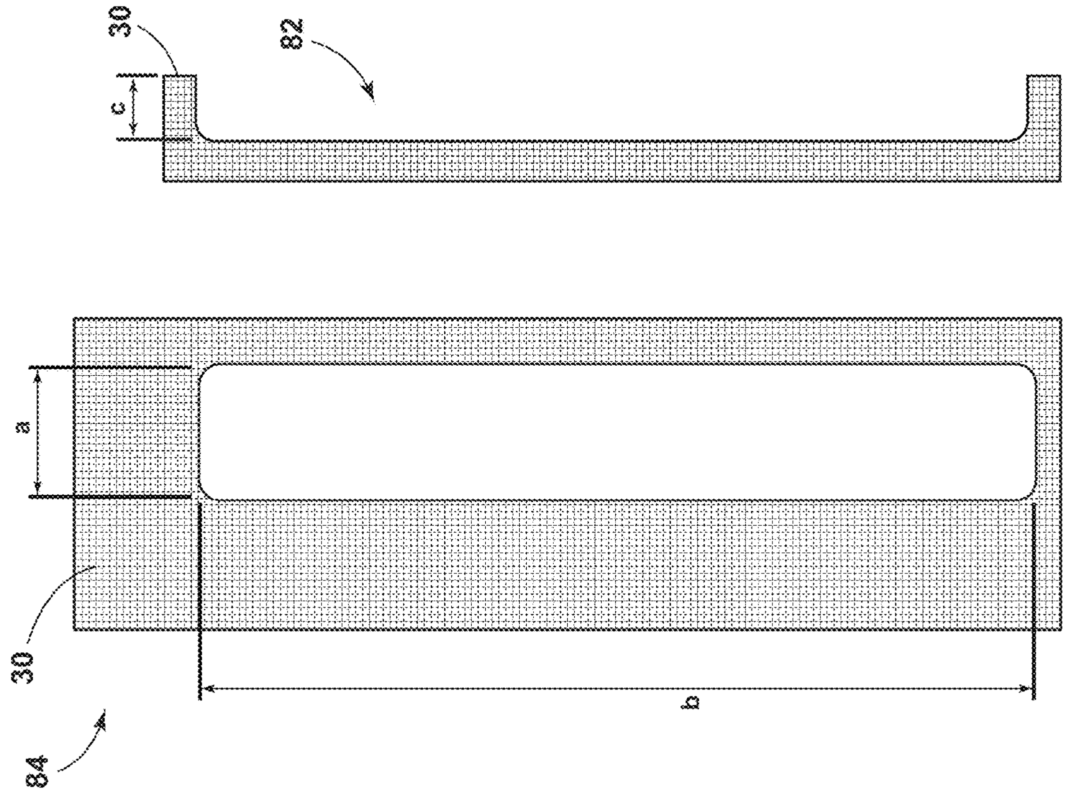
FIG. 4B provides front and side views of a refrigeration cabinet cavity according to some aspects of the present disclosure.
Figure 4A:
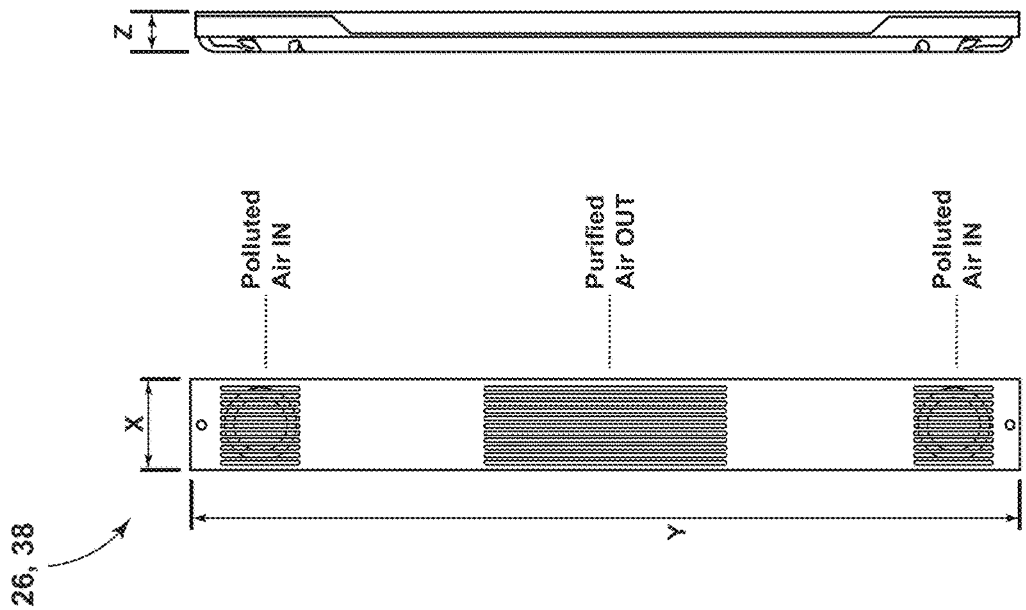
FIG. 4A provides front and side view images of the fan assembly according to some aspects of the present disclosure.

Referring now to FIG. 4A, front and side views of the fan assemblies 26, 38 are provided. In some aspects, the dimensions of the fan assemblies 26, 38 may include a width (X) of about 20 mm to about 60 mm or about 30 mm to about 50 mm. In some aspects, the width (X) of the fan assembly may be about 30 mm, about 40 mm, about 50 mm. The height (Y) of the fan assembly 26, 38 may range from about 200 mm to about 600 mm or about 300 mm to about 500 mm. In some aspects, the height (Y) of the fan assembly may be about 300 mm, about 350 mm, about 398 mm, about 425 mm, or about 450 mm. The depth (Z) of the fan assembly 26, 38 may range from about 5 mm to about 25 mm or about 10 mm to about 20 mm. In some aspects, the depth (Z) of the fan assembly may be about 10 mm, about 15 mm, or about 20 mm. In some aspects, the height (Y) is 398 mm, the width (Z) is about 40 mm, and the depth (Z) is about 16 mm.

Referring to FIG. 4B, the front and side views of the cabinet cavity 82 is provided. In some aspects, the dimensions of the cabinet cavity 82 may include a width (a) from about 20 mm to about 60 mm or from about 30 mm to about 50 mm. In some aspects, the width (a) of the cabinet cavity 82 may be about 30 mm, about 40 mm, or about 50 mm. The height (b) of the cabinet cavity 82 may range from about 200 mm to about 600 mm or from about 300 mm to about 500 mm. In some aspects, the height (b) of the cabinet cavity 82 may be about 300 mm, about 350 mm, about 398 mm, about 425 mm, or about 450 mm. The depth (c) of the cabinet cavity 82 may range from about 5 mm to about 25 mm, or from about 10 mm to about 20 mm. In some aspects, the depth (c) of the cabinet cavity 82 may be about 10 mm, about 15 mm, or about 20 mm. In some aspects, the height (b) is 399 mm, the width is about 41 mm, and the depth is about (c) is about 17 mm.

Figure 5B:
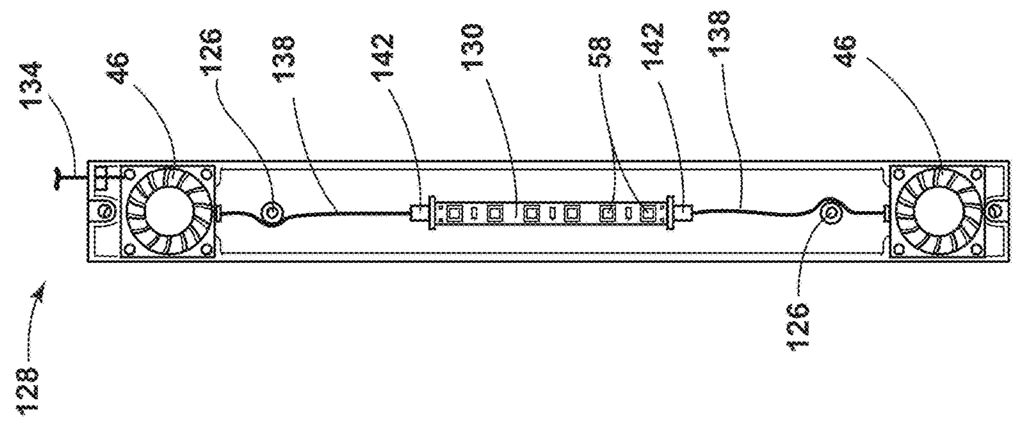
FIG. 5B is a front view of an assembled rear panel assembly according to some aspects of the present disclosure.
Figure 5A:
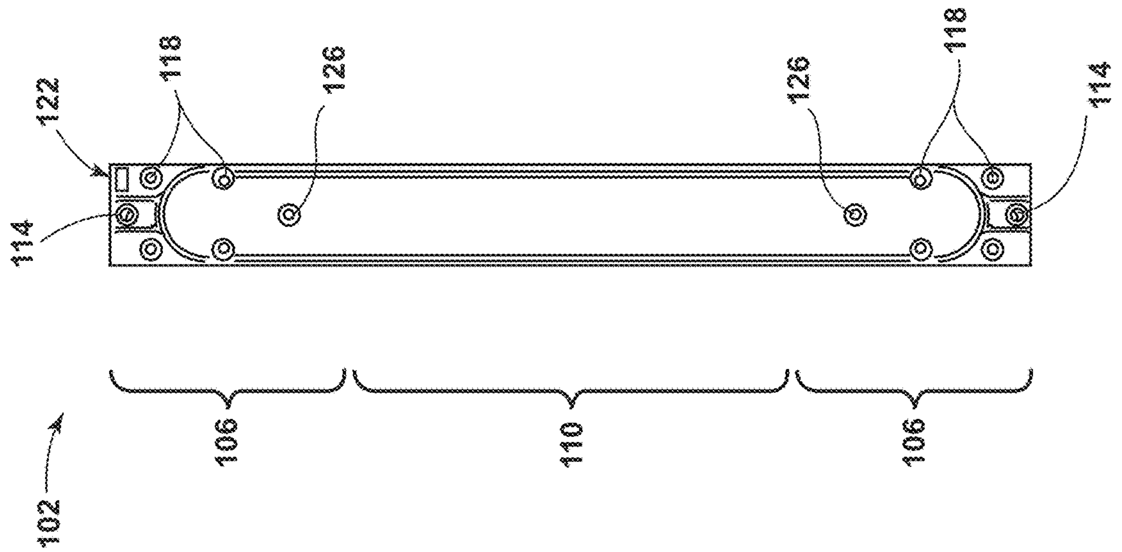
FIG. 5A is a front view of a rear assembly panel according to some aspects of the present disclosure.

Referring now to FIG. 5A, a front view of the rear assembly panel 102 is provided according to some aspect of the present disclosure. The rear assembly panel 102 includes a distal portion 106 at each end of the rear assembly panel 102 and a central portion 110. The rear assembly panel 102 further includes one or more cover fixing members 114, two or more fan fixing members 118, a power cable pass through 122 and an assembly fixing member 126. The one or more cover fixing members 114 may be used to couple the assembly cover panel 146 (see FIG. 6A) when used in combination with one or more coupling members. The coupling members 172 (see FIG. 7) may include any means known in the art used for coupling different members together, for example, but not limited to screws, bolts, nails, clips, snaps, and/or ties. The two or more fan fixing members 118 may be used to couple the two or more circulation fans 46 to the rear panel assembly when used in combination with one or more coupling members 172. The assembly fixing members 126 may be used to couple the rear assembly panel 102 to the cabinet cavity 82 of the storage compartment 22. One or more coupling members 172 may be used in combination with the assembly fixing members 126 to position and retain the rear assembly panel 102 in the cabinet cavity 82.

Referring now to FIG. 5B, a front view of an assembled rear panel assembly 128 is provided. The assembled rear panel assembly 128 includes the rear assembly panel 102 coupled to the circulation fans 46 positioned at each distal portion 106 of the rear assembly panel 102. In addition, the rear assembly panel 102 is coupled to an LED panel 130 having one or more LEDs 58. The one or more LEDs 58 may project visible light, UV-A light, UV-B light, UV-C light, or a combination thereof onto the photocatalyst 54. The assembled rear assembly panel 128 is simplified by being able to weld both an external power supply cable 134 and device wiring 138 to LED conductive tracks 142 of the LED panel 130 and the circulation fans 46. Construction and wiring in this manner allows the assembled rear panel assembly 128 to be achieved using only six tin solders. In some aspects, one or more LED panels 130 having one or more UV LEDs 58 and/or white light LEDs 58 may be coupled and wired into the rear assembly panel 102. For example, in some aspects, the assembled rear panel assembly 128 may include one LED panel 130 having white light LEDS for ambient lighting in the refrigerator 10 and a second LED panel 130 having UV LEDs 58 used to activate the photocatalyst 54 of the activated filter 50 (see FIG. 2). The number of LED panels 130 and/or corresponding LEDs (both UV and other wavelengths) are not meant to be limiting and may be varied depending on the final design and corresponding functionality of the refrigerator 10.

Figure 6B:
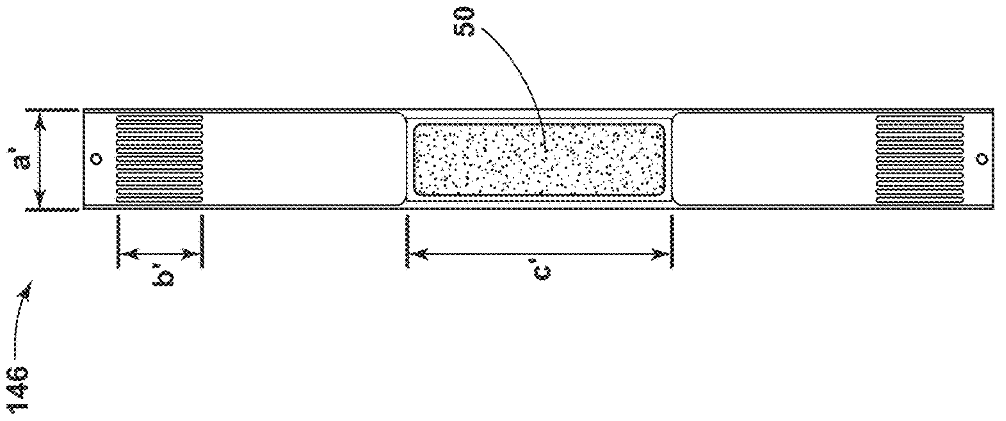
FIG. 6B is a rear view of the assembly cover panel provided in FIG. 6A according to some aspects of the present disclosure.
Figure 6A:
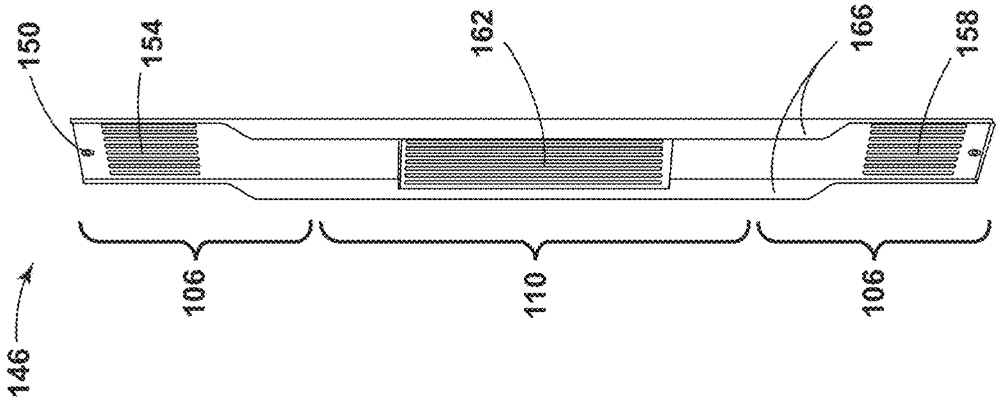
FIG. 6A is a rear isometric view of an assembly cover panel according to some aspects of the present disclosure.

Referring now to FIG. 6A, a rear isometric view of the assembly cover panel 146 is provided. The assembly cover panel 146 includes two distal portions 106 and the central portion 110. The assembly cover panel 146 additionally includes a cover fixing member 150, a first distal vent 154, a second distal vent 158, and a central vent 162. The assembly cover panel 146 also includes two or more side panels 166 to help couple and position the assembly cover panel 146 to the assembled rear panel assembly 102 (see FIG. 5B) in addition to forming side walls.

Referring now to FIG. 6B, a rear view of the assembly cover panel 146 is illustrated coupled to the activated filter 50. In some aspects, the first and second distal vents 154, 158 may have a square shape with a height and width designed to match the size, intake and/or pull of the circulation fans 46. In some aspects, the height and width of the first and second distal vents 154, 158 may range from about 20 mm to about 250 mm, from about 20 mm to about 150 mm, or from about 20 mm to about 50 mm. In some aspects, the height and width of the first and second distal vents 154, 158 may be about 50 mm, about 40 mm, or about 30 mm. The length of the activated filter may range from about 100 mm to about 130 mm. In some aspects, the activated carbon filter may have a length of about 115 mm and a width of about 38 mm. The shape and associated dimensions of the distal vents 154, 158 and central filter vent 162 are not meant to be limiting and may be changed to meet the desired design and properties of the refrigerator 10.

Figure 7:
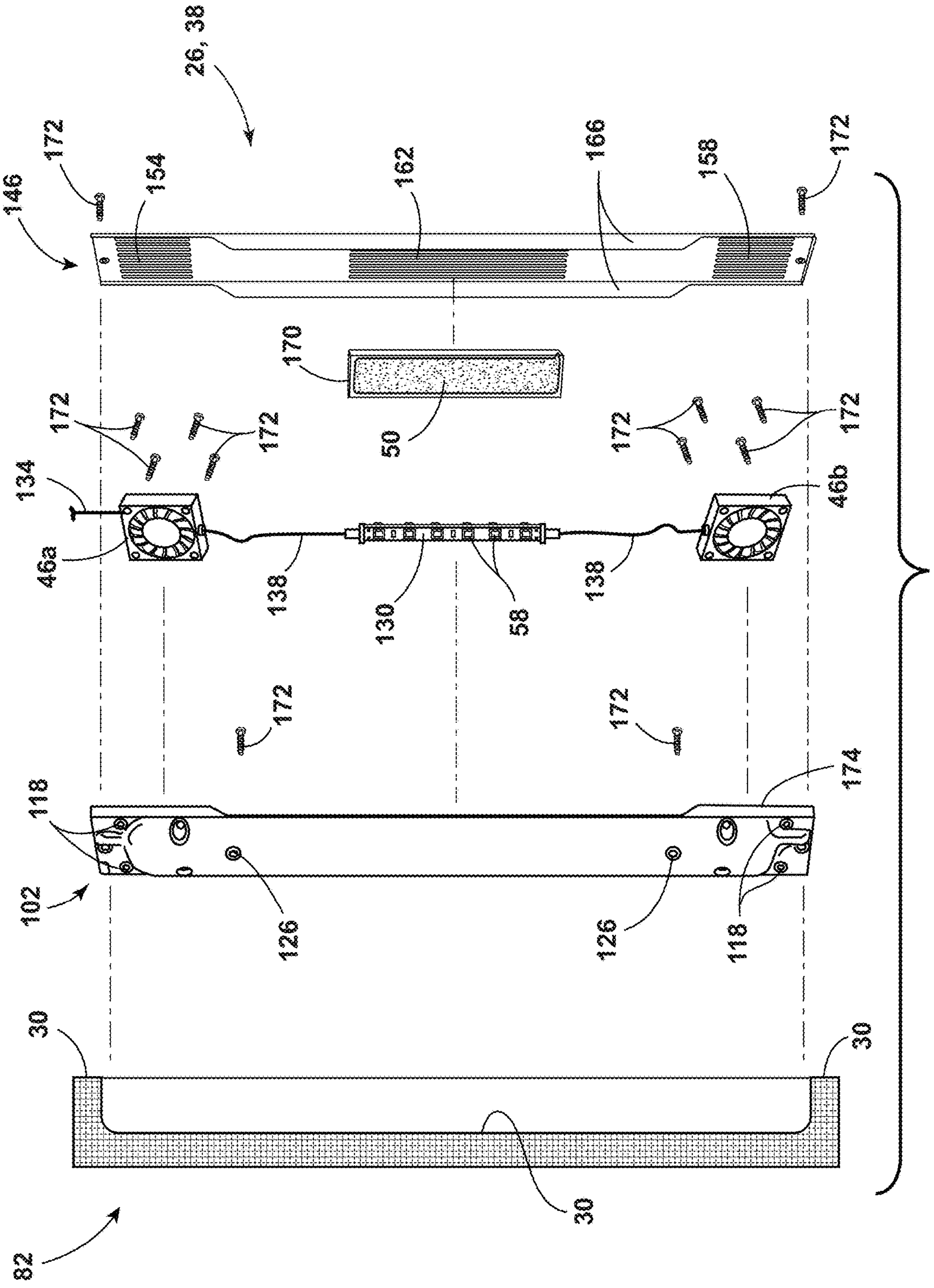
FIG. 7 is an exploded side view of a fan assembly and refrigeration liner according to some aspects of the present disclosure.

Referring now to FIG. 7, an exploded side view of the fan assemblies 26, 38 and corresponding refrigeration liner 82 is provided. As illustrated, the assembly cover panel 146 is coupled to the activated filter 50. In some aspects, the activated filter 50 may include a framing member 170 used to stabilize the edges of the activated filter 50 and facilitate coupling of the activated filter 50 to the assembly cover panel 146. A first circulation fan 46*a* and a second circulation fan 46*b* are coupled to the rear assembly panel 102 through the fan fixing members 118 and coupling member 172 in addition to the LED panel 130 including the plurality of LEDs 58. The side panels 166 and end side panels 174 are positioned with respect to each other to butt up against each other to form a uniform side wall for the fan assemblies 26, 38. The fan assemblies 26, 38 are then positioned into the cabinet cavity 82 where the fan assembly 26, 38 may be positioned flush with the interior surface 30 of the cabinet walls 34, 42 or refrigerator doors 18*a*, 18*b* (see FIG. 1D). In some aspects, the cabinet cavity 82 may be coupled to a flat interior surface 30 on the cabinet walls 34, 42 where the installed fan assemblies 26, 38 would stick out from the interior surface 30 to form a ledge or protrusion from the cabinet walls 34, 42. In other aspects, the cabinet cavity 82 may be a cutout or indentation in the cabinet walls 34, 42 where the interior surface 30 forms an indentation formed to receive the fan assemblies 26, 38 to form an even or flat surface on the cabinet walls 34, 42. In some aspects, the first and second fan assemblies 26, 38 are each positioned in the cabinet cavity 82 on the interior surface 30 of the first and second cabinet walls 34, 42. In other aspects, the first and second fan assemblies 26, 38 may each be positioned on a front lip or edge of the cabinet cavity 82 on the interior surface 30 of the first and second cabinet walls 34, 42 configured to direct the air circulation path 62 (see FIG. 2) and corresponding fresh outside air into the first and second fan assemblies 26, 38 before entering the cabinet cavity 82.

The activated filter 50 may be formed by coating, coupling, and/or adsorbing the photocatalyst 54 onto a filter. In some aspects, the filter or filter membrane may be made from a polymer fiber, a glass fiber, a ceramic fiber, or a combination thereof. The polymer fiber may include polyethylene (PE), polypropylene (PP), polyester, polyamide, polyvinylpolypyrrolidone (PVPP), polystyrene, polyimides, naturally occurring polymers, thermoplastics, thermosets, or combinations thereof. In some aspects, the polymer fiber used to make the filter is polyethylene or a blend of polyethylene. In some aspects, wherein the activated filter 50 is a polymeric filter coupled to a UV activated photocatalyst. The photocatalyst 54 and UV activated photocatalyst may include titanium dioxide ($TiO_2$), zinc oxide (ZnO), tin oxide ($SnO_2$), cesium oxide ($CeO_2$), zinc titanium dioxide ($ZnTiO_2$), copper titanium dioxide ($CuTiO_2$), silver titanium dioxide ($AgTiO_2$), iron titanium dioxide ($FeTiO_2$), or combinations thereof. In some aspects, the photocatalyst 54 includes titanium dioxide ($TiO_2$). The photocatalyst 54 may be coated, coupled, and/or adsorbed onto the filter using a variety of techniques including, for example, a sol gel approach. In some aspects, the activated filter 50 includes a polyethylene filter having a photocatalytic titanium dioxide ($TiO_2$) film deposited on its surface forming a nanostructured $TiO_2$ layer using sol gel. In other aspects, the activated filter 50 may further include an activated carbon and/or carbon black particles used to help filter the polluted air. In some aspects, the activated filter 50 is an activated carbon filter coupled to a titanium oxide ($TiO_2$) doped sol gel. The $TiO_2$ or other photocatalyst 54 doped sol gel may include any sol gel or sol gel technique or method known in the art. In some aspects, the rear assembly panel 102 and the assembly cover panel 146 may both be coupled to the photocatalyst 54 to provide an activated surface. The photocatalyst 54 may be operatively coupled to the rear assembly panel 102 and/or the assembly cover panel 146 using sol gel techniques or any other coating applications known by one skilled in the art (e.g., spin coating, solvent evaporation, spray coating, brushing, etc.).

The LEDs 58 mounted on the LED panel 130 may be positioned or spaced apart from the activated filter 50 by from about 0.5 cm to about 4 cm or from about 1 cm to about 3 cm. In some aspects, the LEDs 58 may be spaced apart from the activated filter 50 by about 0.5 cm, about 1 cm, about 1.5 cm, about 2 cm, about 2.5 cm, about 3 cm, about 3.5 cm, or about 4 cm. In some aspects, the LED panel 130 and corresponding LEDs 58 may be mounted or positioned directly in front of the activated filter 50 having the photocatalyst 54. In some aspects, the LEDs 58 generate UV light that can kill bacteria without the use of the photocatalyst 54. In other aspects, the photocatalyst 54 is activated when exposed to UV and/or visible light generated and projected by the LEDs 58 where the activated photocatalyst 54 may be able to kill and/or damage the bacteria. In some aspects, the LEDs 58 can project a wavelength from about 100 nm to about 405 nm, from about 250 nm to about 405 nm, from about 280 nm to about 405 nm, from about 315 nm to about 405 nm, from about 365 nm to about 405 nm, or from about 395 nm to about 405 nm. In some aspects, the plurality of LEDs 58 are UV-A LEDs that are positioned to project UV-A light on the activated filter 50. In other aspects, the plurality of LEDs 58 are UV-B LEDs that are positioned to project UV-B light on the activated filter 50. In still other aspects, the plurality of LEDs 58 are UV-C LEDs that are positioned to project UV-C light on the activated filter 50. In some aspects, the plurality of LEDs 58 are positioned to project UV-A light (315 nm to 400 nm), UV-B light (280 nm to 315 nm), UV-C light (100 nm to 280 nm), or a combination thereof on the activated filter 50. In other aspects, the LEDs 58 may project UV-A, UV-B, UV-C, or a combination of light thereof and/or visible light in the range from about 400 nm to about 700 nm. In still other aspects, the LEDs 58 may project visible light in the range from about 400 nm to about 700 nm.

Figure 9A:
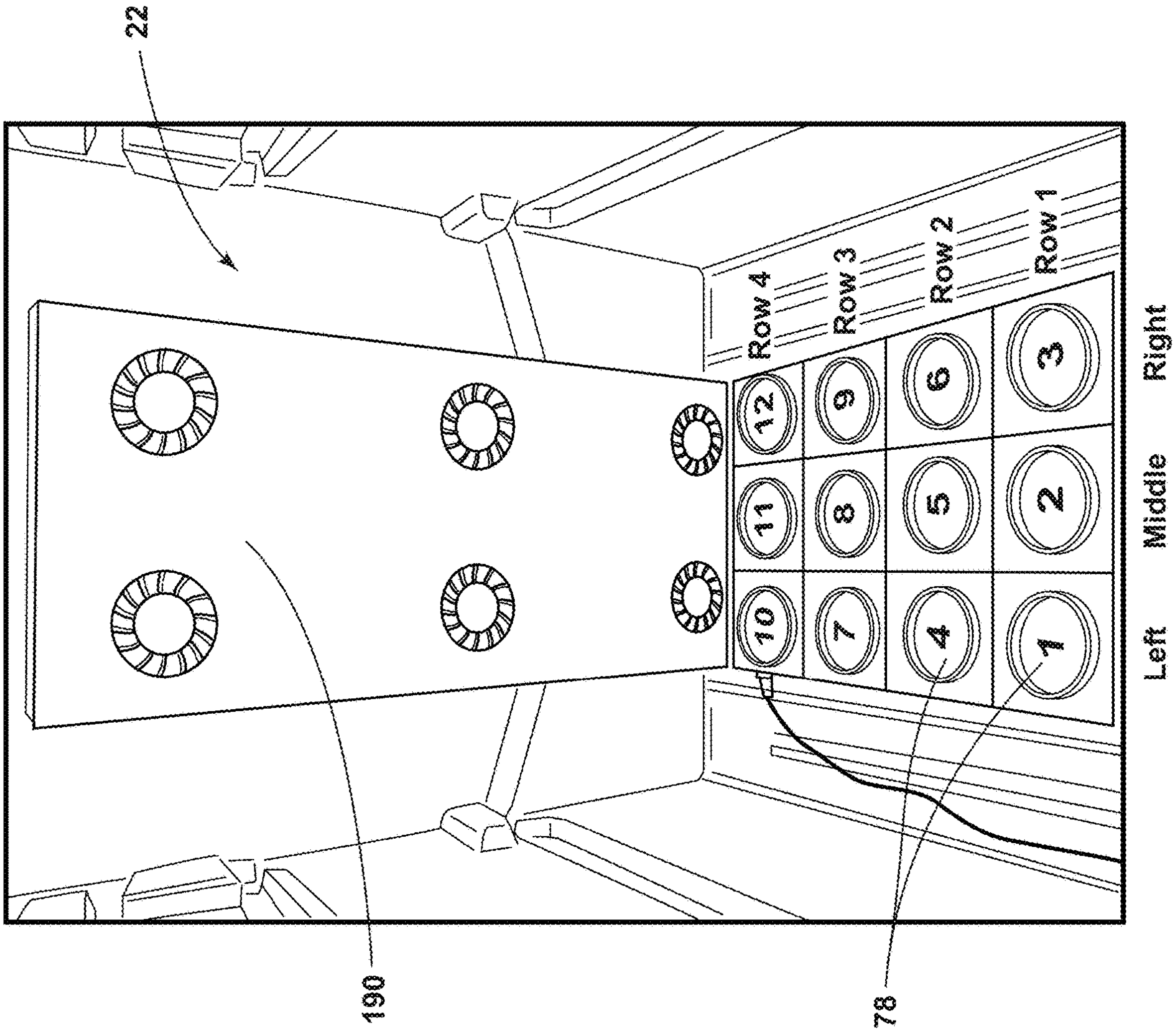
FIG. 9A is a picture of the experimental set up of the nebulization of an inoculum solution using a fan assembly for fan filtration according to some aspects of the present disclosure.
Figure 9B:
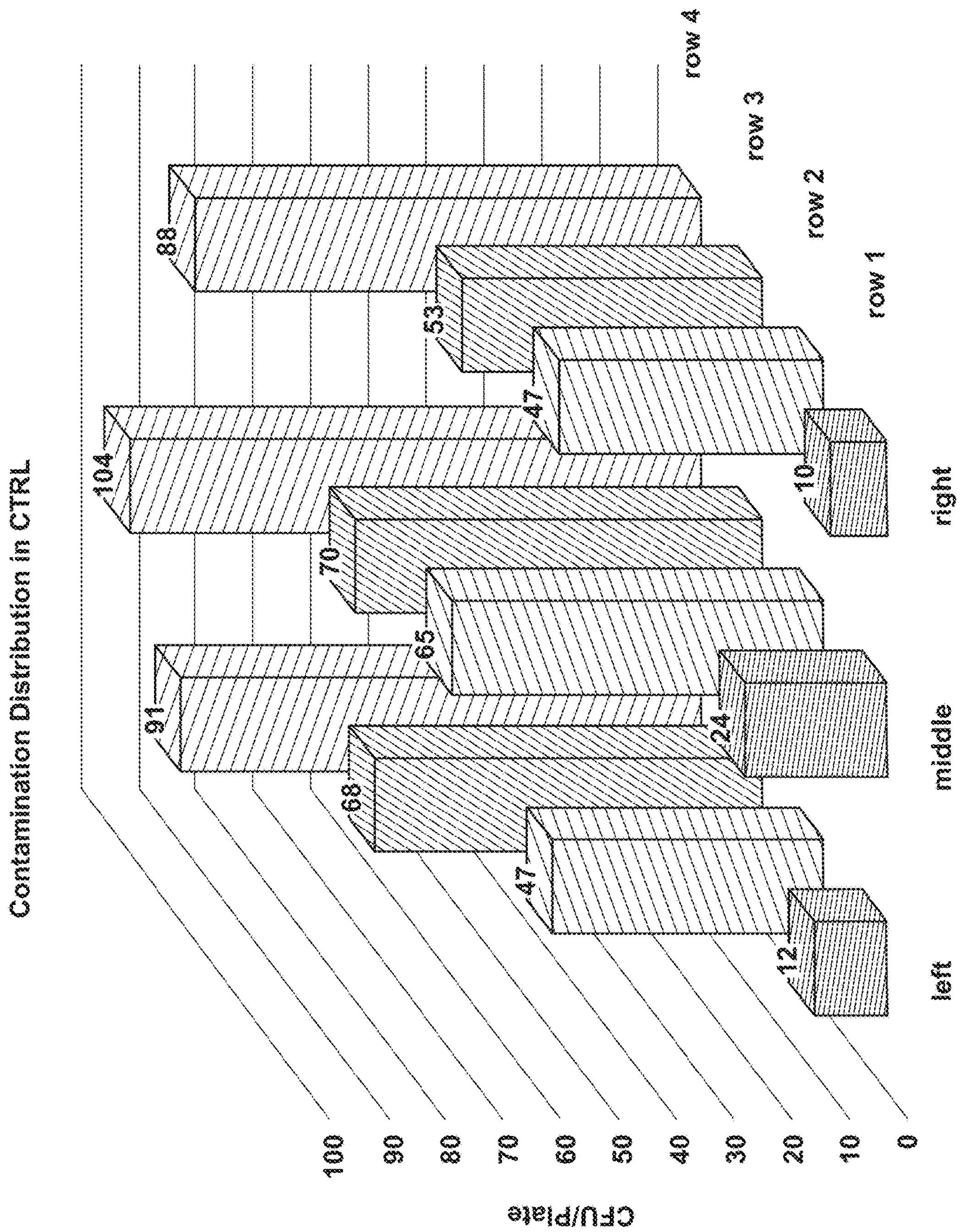
FIG. 9B is a distribution of microbial populations in a control using one fan assembly.
Figure 9C:
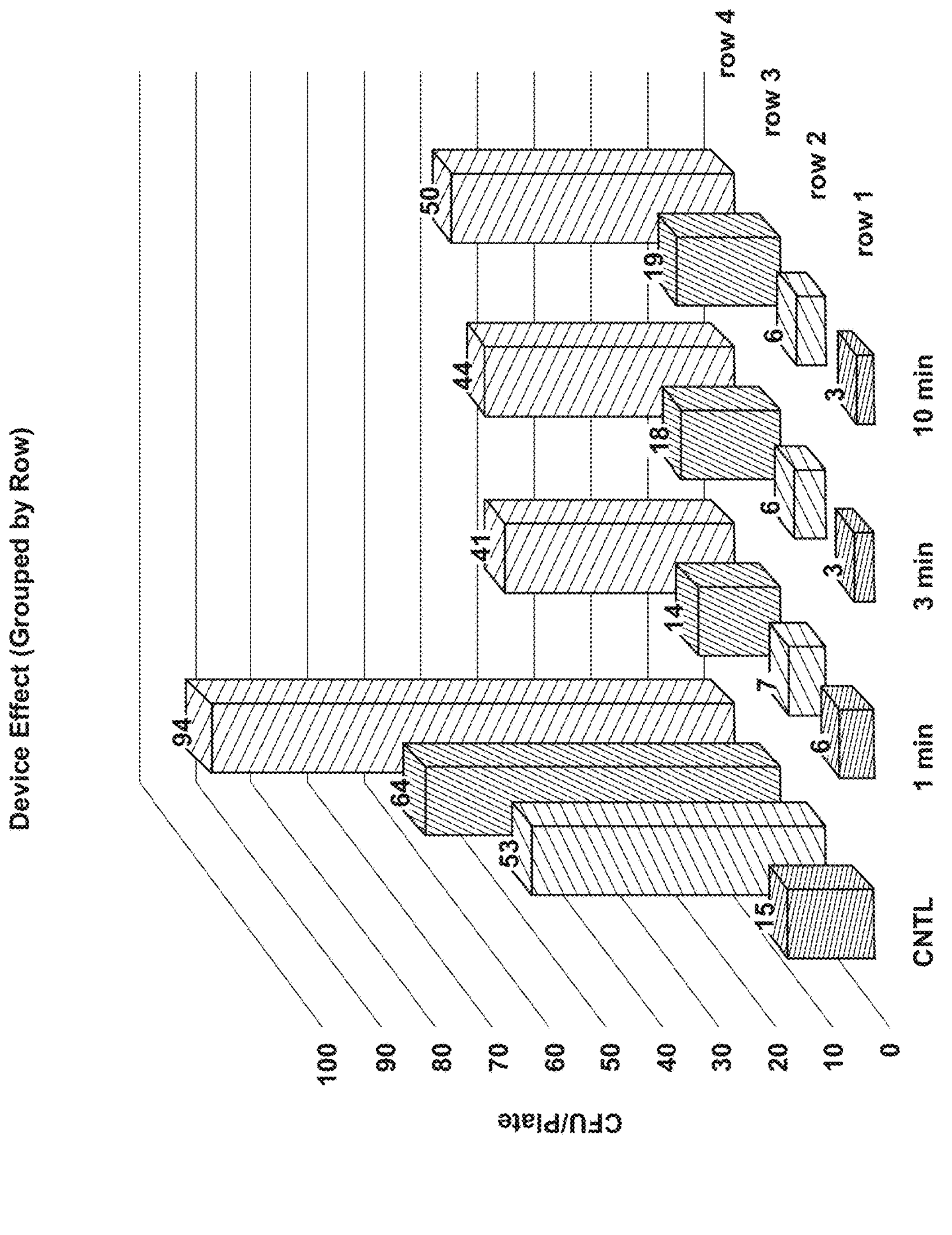
FIG. 9C provides averages of the distribution of microbial populations at various different times.

As will be provided in more detail in the description for FIGS. 9A-9C, two or more fan assemblies 26, 38 may be required to provide the air circulation path 62 necessitated to remove a higher percentage of airborne bacteria 66, particulate matter 70, volatile organic compounds (VOCs), and molds from the storage compartment 22 of the refrigerator 10. As provided in FIGS. 1C, 9B, and 9C, the use of just one circulation fan or fan assembly may be unable to provide an air circulation path that can effectively eliminate enough of the airborne bacteria 66 and particulate matter 70. In some aspects, two or more fan assemblies 26, 38 may be positioned on opposing first and second cabinet walls 34, 42, positioned on the first and second doors 18*a*, 18*b*, or positioned on any two opposing interior surfaces where the first and second fan assemblies 26, 38 work in a complementary manner to provide the improved air circulation path 62. In some aspects, the first and second cabinet walls 34, 42 are opposing walls or walls that are facing each other to complementary circulate the air present in or coming into the storage compartment 22. The air circulation path 62 may better direct the airborne bacteria 66, particulate matter 70, volatile organic compounds (VOCs), and molds into the first and second fan assemblies 26, 38 to be filtered. In some aspects, the first cabinet wall 34 opposes the second cabinet wall 42. In some aspects, the air circulation path 62 is configured to direct bacteria throughout the central area of the storage compartment 22

Unlike the limited filtering ability provided using the single standard filtration system 80 (see FIG. 1C), the combination of the first and second fan assemblies 26, 38 are configured to provide the air circulation path 62 that directs the airborne bacteria 66, particulate matter 70, volatile organic compounds (VOCs), and/or molds simultaneously or contemporaneously into the fan assemblies 26, 38 using the two or more circulation fans 46 to direct the polluted air through the activated filter 50 irradiated by UV and/or visible light projected from the LEDs 58 to filter and clean the polluted air to circulate filtered air into the storage compartment 22 of the refrigerator 10. In some aspects, the two or more circulation fans 46 are configured to direct the air circulation path 62 in through the two or more circulation fans 46 and out through the activated filter 50 where the air circulation path 62 is configured to direct bacteria positioned in the central area of the storage compartment 22 into the first and second fan assemblies 26, 38.

Although the various aspects of the fan assemblies 26, 38 disclosed herein generally direct the air circulation path 62 into the fan assemblies 26, 38 using the two or more circulation fans 46, in other aspects, the two or more circulation fans 46 are configured to direct the air circulation path 62 in through the activated filter 50 and out through the two or more circulation fans 46. The reversal of the air circulation path 62 is considered to be within the scope of the disclosure of the present invention.

In some aspects, the first and second fan assemblies 26, 38 are able to provide at least a 50% microbial reduction in one minute, at least a 50% microbial reduction in three minutes, or at least a 50% microbial reduction in ten minutes. In other aspects, the first and second fan assemblies 26, 38 are able to provide at least a 60% microbial reduction in one minute, at least a 60% microbial reduction in three minutes, or at least a 60% microbial reduction in ten minutes. In still other aspects, the first and second fan assemblies 26, 38 are able to provide at least a 70% microbial reduction in one minute, at least a 70% microbial reduction in three minutes, or at least a 70% microbial reduction in ten minutes. In other aspects, the first and second fan assemblies 26, 38 are able to provide at least an 80% microbial reduction in one minute, at least an 80% microbial reduction in three minutes, or at least an 80% microbial reduction in ten minutes.

Figure 8A:
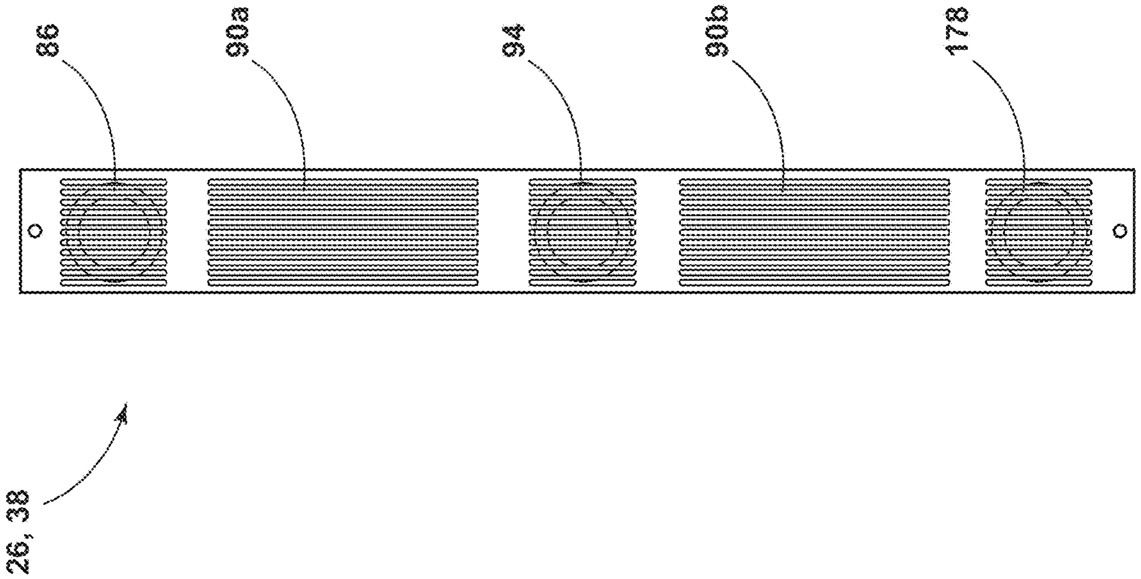
FIG. 8A is a front view of an alternative embodiment of a fan assembly according to some aspects of the present disclosure.

Referring now to FIG. 8A, a front view of an alternative aspect of the fan assemblies 26, 38 is provided. The fan assemblies 26, 38, according to other aspects of the current disclosure, may include the first intake 86, a first exhaust 90*a*, the second intake 94, a second exhaust 90*b*, and a third intake 178. In some aspects, the number of intakes and the number of exhausts may be limited to the number of circulation fans 46 and activated filters 50 incorporated into the fan assembly 26, 38 based on the design and/or final air circulation properties desired for the refrigerator 10. In some aspects, the number of intakes may be two, three, four or more while the number of exhausts may include one, two, three, four, or more where the intakes and exhausts may be positioned with respect to each other in any combination.

Figure 8B:
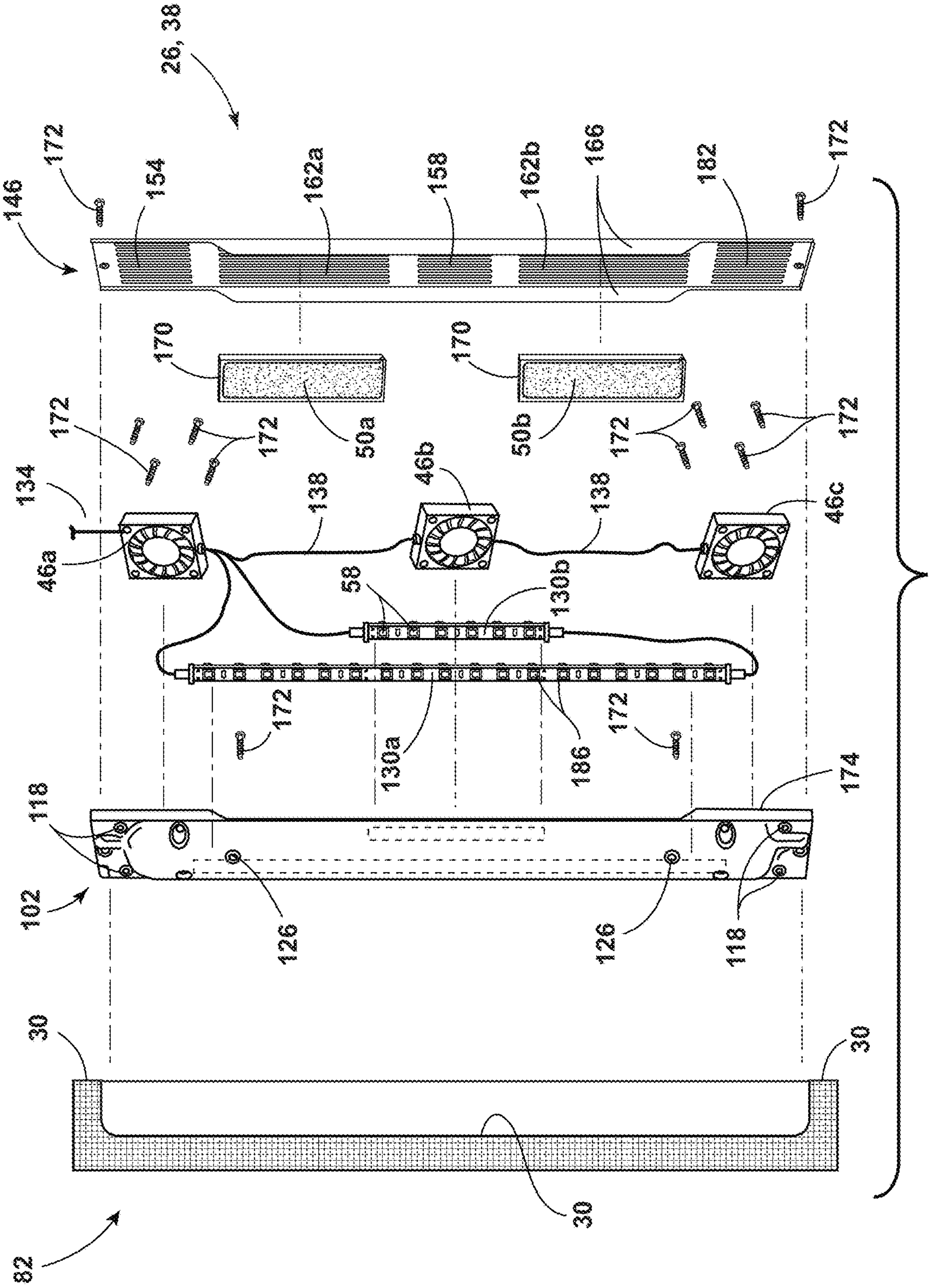
FIG. 8B is an exploded side view of the fan assembly provided in FIG. 8A according to some aspects of the present disclosure.

Referring now to FIG. 8B, an exploded side view of the fan assemblies 26, 38 provided in FIG. 8A and corresponding refrigeration liner 82 is provided. As illustrated, the assembly cover panel 146 is coupled to two activated filters 50*a*, 50*b* having framing members to stabilize the edges and facilitate coupling of the activated filters 50*a*, 50*b* to the assembly cover panel 146. The assembly cover panel 146 includes a first fan vent 154, a first filter vent 162*a*, a second fan vent 158, a second filter vent 162*b*, and a third filter vent 182. The first circulation fan 46*a*, second circulation fan 46*b*, and a third circulation fan 46*c* are coupled to the rear assembly panel 102 using coupling members 172 in addition to a first LED panel 130*a* having a plurality of white light LEDs 186. In addition, a second LED panel 130*b* having the plurality of UV LEDs 58 is also positioned on the rear panel assembly 102 to project UV light on the photocatalyst 54 of the activated filters 50*a*, 50*b*. The side panels 166 and end side panels 174 are positioned up against each other to form solid siding portions for the fan assemblies 26, 38. The fan assemblies 26, 38 may be then positioned into the cabinet cavity 82 where the fan assembly 26, 38 may be positioned flush with the interior surface 30 of a cabinet wall 34, 42 or refrigerator doors 18*a*, 18*b*.

According to another aspect of the present disclosure, an air purifying fan assembly 26 is provided. The air purifying fan assembly 26 includes the rear assembly panel 102 and the assemble cover panel 146. The assemble cover panel 146 includes one or more air intakes 86, 94 and one or more air exhausts 90*a*, 90*b*; one or more circulation fans 46 positioned inside the rear assembly panel 102 and the assemble cover panel 146 and adjacent to the one or more air intakes 86, 94 or one or more air exhausts 90*a*, 90*b*; one or more activated filters 50 having a sol gel photocatalyst 54 and the activated carbon. The activated filter 50 is positioned in line or directly across from the one or more air exhausts and one or more LEDs 58 positioned to project light on the activated filter 50.

It is understood that the descriptions outlining and teaching the first and second fan assemblies 26, 38 previously discussed, which can be used in any combination, apply equally well to the air purifying fan assembly 26 described herein.

EXAMPLES

The following examples and their corresponding data represent certain non-limiting examples of the first and second fan assemblies 26, 38 used in conjunction with each other to effectively filter air in the storage compartment 22 of the refrigerator 10.

Materials

All chemicals, bacteria, growth media, and other constituents were obtained from commercial suppliers and used as provided.

The antibacterial refrigerator 10 and its corresponding air purifying assemblies defined by the fan assemblies 26, 38 and/or the air purifying duct assembly 192 are designed to remove contaminants such as odor, toxic particles, and pathogens. Examples of key substances that are typically removed through this air-treatment process include parasites, bacteria, algae, viruses, fungi, ethylene, and other food related chemical pollutants.

Air Circulation and Fan Positioning Examples

Referring now to FIGS. 9A-9C, a description of the experimental set up for the nebulization of an inoculum solution using the fan assemblies 26, 38 for air filtration in the storage compartment 22 is provided. The inoculum solution used in the experiments illustrated in FIG. 9A includes a microbial-loaded saline solution (50-70 ml) recovered during hand washing procedures. To quantify the overall microbial load of the test inoculum, the count of viable microorganisms was determined by means of the pour plate culture method. Briefly, the number of viable microorganisms was counted on Luria-Bertani broth (LB) agar petri dishes (θ=60 mm) after serial ten-fold dilutions of the test inoculum suspensions and plating. Plating was performed in duplicate, and the number of viable microorganisms was determined according to the following equation: $N=(C \times D)/V$ where N=number of viable bacteria per ml; C=average plate count for the duplicate plates (e.g., number of colony forming units, CFU, determined in each LB-agar plate); D=dilution factor for the plate counted; and V=volume of test inoculum (in ml).

As illustrated in FIG. 9A, the inner compartment of a refrigerator (Whirlpool, BLFV8121W model) and the antibacterial device were first cleaned to remove any gross contamination using a quaternary benzyl ammonium disinfectant where the same cleaning procedure was performed on the storage compartment 22 in between each experiment.

Following the cleaning procedure, the antibacterial device was placed inside the refrigerator and the refrigerator was left to equilibrate at 40° C. for at least 24 hours. Before nebulization of the inoculum solution was provided, 12 sterile LB-agar petri dishes 78 (θ=60 ml, N=12) were placed inside the refrigerator compartment. The experiments included the nebulization of 450 microliters (μL) of inoculum inside the refrigerator through a small hole made on the front wall of the refrigerator door (θ=1.2 cm). Immediately upon the nebulization of the inoculum solution, a test air filtration device 190 was switched on and kept running for a variety of different time periods (e.g., 1 min, 3 min, 10 min) after a microbial nebulization. Control experiments were carried out in the same conditions, but the test air filtration device 190 was not activated. In each of the experiments, the LB-agar petri dishes 78 were closed about 10 minutes after the microbial nebulization and incubated for the first 24 hrs at 37° C., and then for an additional 48 hrs at room temperature (RT). The number of viable microorganisms was then counted on LB-agar petri dishes. All of the experiments noted were performed in triplicate. Data was normalized with respect to the number of viable counts and control samples (CTRL, e.g., air filtration device turned off), considering the number of microorganisms in such condition as 100%. Results are expressed as mean±standard deviation (SD).

Referring now to FIG. 9B, the distribution results of the microbial population measured in colony forming units (CFU) for the cultured control experiments are provided. A homogeneous distribution was found for each respective row, which seemed to be dependent on the distance from the nebulization inlet port and/or the test air filtration device 190. When the test air filtration device 190 was permitted to run for longer durations, the number of microorganisms decreased from about 50% eliminated to about 75% eliminated after one minute, and this decrease in CFU was maintained over time. This corresponding decrease was shown to be at least partly dependent on the distance from the test air filtration device 190. The row of LP-agar petri dishes 78 positioned closest to the test air filtration device 190 (Row 4) contained the highest microbial population relative to Rows 1-3 while lowest microbial population was observed in the row furthest from the test air filtration device 190 (Row 1). The uniform difference and disparity in microbial populations based on the difference in distance between the corresponding rows and the test filtration device 190 supports the need for two or more air filtration devices 26, 38 as described herein.

Referring now to FIG. 9C, the viable CFU counts for each of the four rows (Rows 1-4) were averaged and plotted against time as the test air filtration device 190 was operated to filter the storage compartment 22. Consistent with the data provided in FIG. 9B, when the filtration device was run for a longer period of time (e.g., 10 min vs. 3 min vs 1 min), the number of microorganisms decreased from about 50 to about 75% already after one minute and was generally maintained over the longer periods of time. Again consistent with the data provided in FIG. 9B, the decrease in CFU counted is dependent on the distance from the test air filtration device 190 where the decrease in CFU was more pronounced or greater at distances further away from the test air filtration device 190.

Filter Reduction of Microbial Populations

Figure 10:
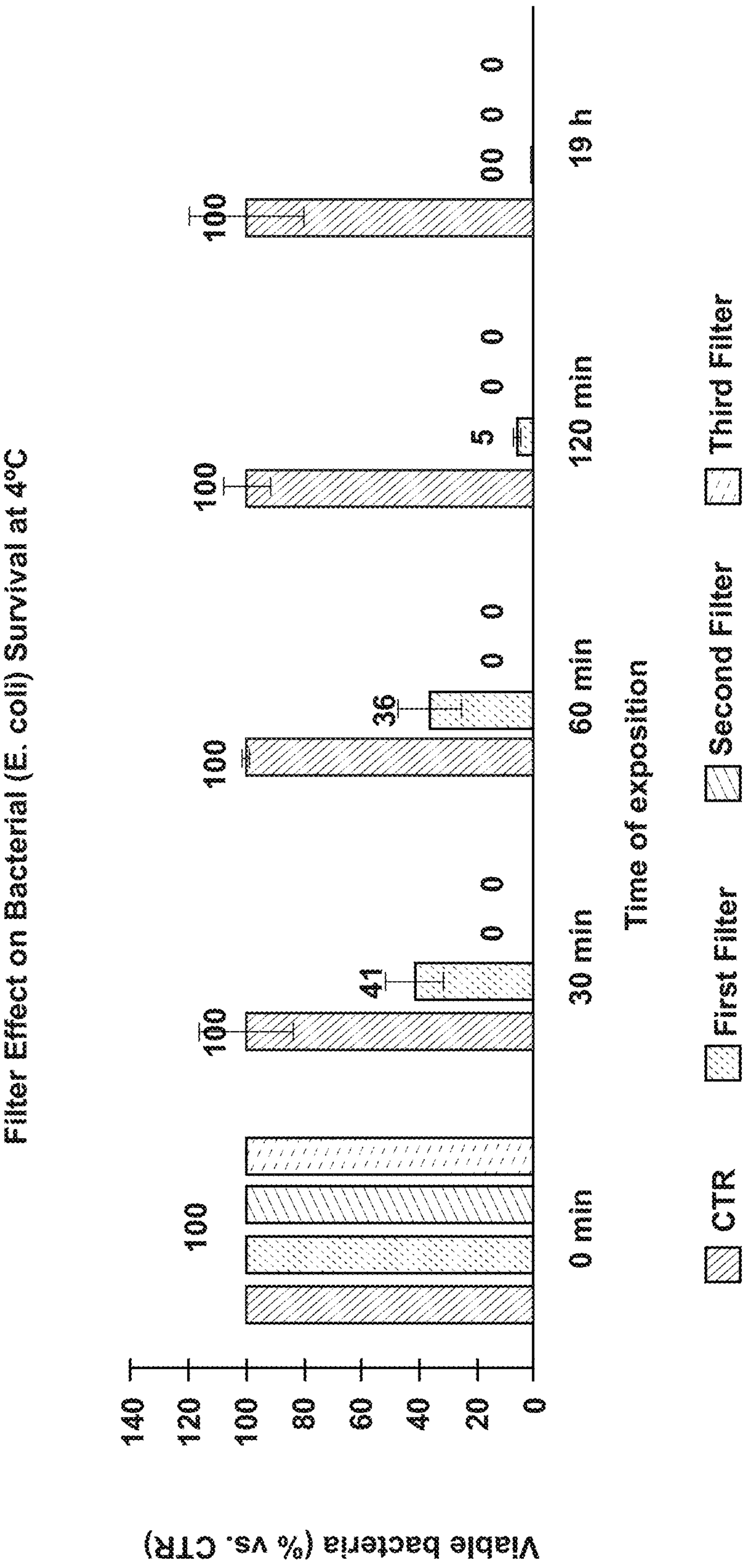
FIG. 10 is a quantification of viable bacteria after incubation with different air filters at different time intervals.

Referring now to FIG. 10, an assessment of the in vitro time-dependent reduction of a microbial population after exposure to different activated filters 50 having the photocatalyst 50 including a $TiO_2$ doped sol gel. The antibacterial effectiveness of a variety of filters was assessed using three different filters: 1) Filter 1, a polymeric filter having no photocatalyst 50 incorporated, 2) Filter 2, a polymeric filter treated with a first $TiO_2$ doped sol gel as the photocatalyst 50; and 3) Filter 3, a polymeric filter treated with a second $TiO_2$ doped sol gel as the photocatalyst 50. The activated filters 50 were put in contact with *E. coli* Gram-negative bacteria that, together with *Pseudomonas* and *Salmonellas*, are well-known food contaminants. All the experiments were performed according to the ASTM E 2315 and ISO 22196 international standards with minor modifications as described herein. For example, the bacterial load was increased in order to mimic the effect of the long-term exposure to food contaminants. The antibacterial activity of the devices was assessed at 4° C. and at some sampling intervals (i.e., 30 min, 60 min, 120 min, and 19 h). The results demonstrated that Filters 2 and 3 were found fully effective in killing all detectable bacteria within 30 minutes of incubation. In addition, antimicrobial efficiency was also displayed for Filter 1 although a slower kinetic pattern was observed relative to Filters 2 and 3.

The study was performed using three different air filters/devices: 1) Filter 1; 2) Filter 2; and 3) Filter 3. Disc-shaped specimens (Ø=15 mm, surface area=1.75 cm2) were cut from each kind of polymeric filter and transferred into a sterile 24-well plate.

An aliquot of Gam-negative *E. coli* (strain JM109, cat. 53323, ATCC) was transferred onto a sterile Lysogeny broth agar (LB-A) plate and incubated at 37° C. for 20 hrs to allow bacterial colonies to grow. After incubation, using a sterile inoculating loop, a single colony was transferred into a 50 mL polypropylene tube (Corning) filled with 5 mL of sterile LB liquid growth medium and incubated overnight (ON) at 37° C. under shacking, to produce sufficient microbial suspension. The number of bacteria within the microbial suspension was roughly estimated by measuring the optical density of the suspension at λ=600 nm ($OD_{600\ nm}$) by means of a Nanodrop 2000 spectrophotometer (Thermo Scientific). Afterwards, the inoculum was prepared diluting the microbial suspension in sterile LB to an $OD_6OD_{600\ nm}$=0.02. Bacteria were next allowed to grow until they reached an $OD_{600\ nm}$=0.6 (exponential growth phase). The inoculum was finally centrifuged for 10 min at 4,000 g, washed once in sterile deionized water (dH2O), pelleted again and the cells suspended in dH2O to give a bacterial concentration of ≈5×$10^8$ bacteria/mL.

Following a pre-incubation at 4° C., the test specimens were brought into contact with the inoculum suspension. The experiments were carried out according to the ASTM E 2315 (Assessment of Antimicrobial Activity Using a Time-Kill Procedure) [1] and ISO 22196 (Measurement of antibacterial activity on plastics and other non-porous surfaces) [2] standards, with slight modifications that are in the $10^8$ times higher bacterial load and the temperature at which the experiments were performed (e.g., 4° C. instead of 35±1° C.).

Each test specimen (Filter 1 samples, n=3; Filter 2, n=2; Filter 3, n=2) was inoculated with 1 mL of the bacterial inoculum and incubated at 4° C. for different durations (i.e., 30 min, 60 min, 120 min and 19 h). During the experiments, the Filters 2 and 3 having the photocatalyst 54 added using a sol gel approach underwent UV irradiation (i.e., the final device setup). Bacteria inoculated in wells without any filter were used as positive controls (untreated bacteria).

At different time intervals, a 30 μL aliquot of bacterial suspension kept in contact with the test specimens was removed from each well, serially diluted in sterile dH2O (1:10, 1:100, 1:1,000), plated onto LB-A P60 plates and incubated ON at 37° C. to allow bacterial colonies to grow. After incubation, the number of viable bacteria was evaluated by counting the colony forming units (CFU) grown on agar plates. The number of viable cells was standardized to the plated area ($cm^2$) and the dilution factor. Finally, data were normalized with respect to the number of viable cells in control samples at each time step, considering the number of untreated bacteria as 100%. Results were expresses as mean±standard error of means (SEM).

The antibacterial effectiveness of the three filters/devices was evaluated using the Time-Kill procedure, assessed by measuring the reduction of the microbial population over time. The results are illustrated in FIG. 10. Upon analyzing the graph, the highest antimicrobial activity was observed for the Filter 2 and 3 activated filters 50 having the photocatalyst 54. After 30 min of incubation for Filters 2 and 3, no viable bacteria was detected. As the maximum efficiency was found at the shortest duration, this antibacterial behavior was maintained thereafter for Filters 2 and 3. A time-killing effect was observed for the Filter 1 samples, although when in contact with this kind of filter having no active photocatalyst incorporated, the number of viable cells decreased up to ≈40% already after 30 min of incubation, and it dropped to 5% after 120 min. After 19 hrs of incubation, only 0.2% of bacteria were viable.

Reduction of Volatile Organic and Particulate Matter Examples

Figure 11A:
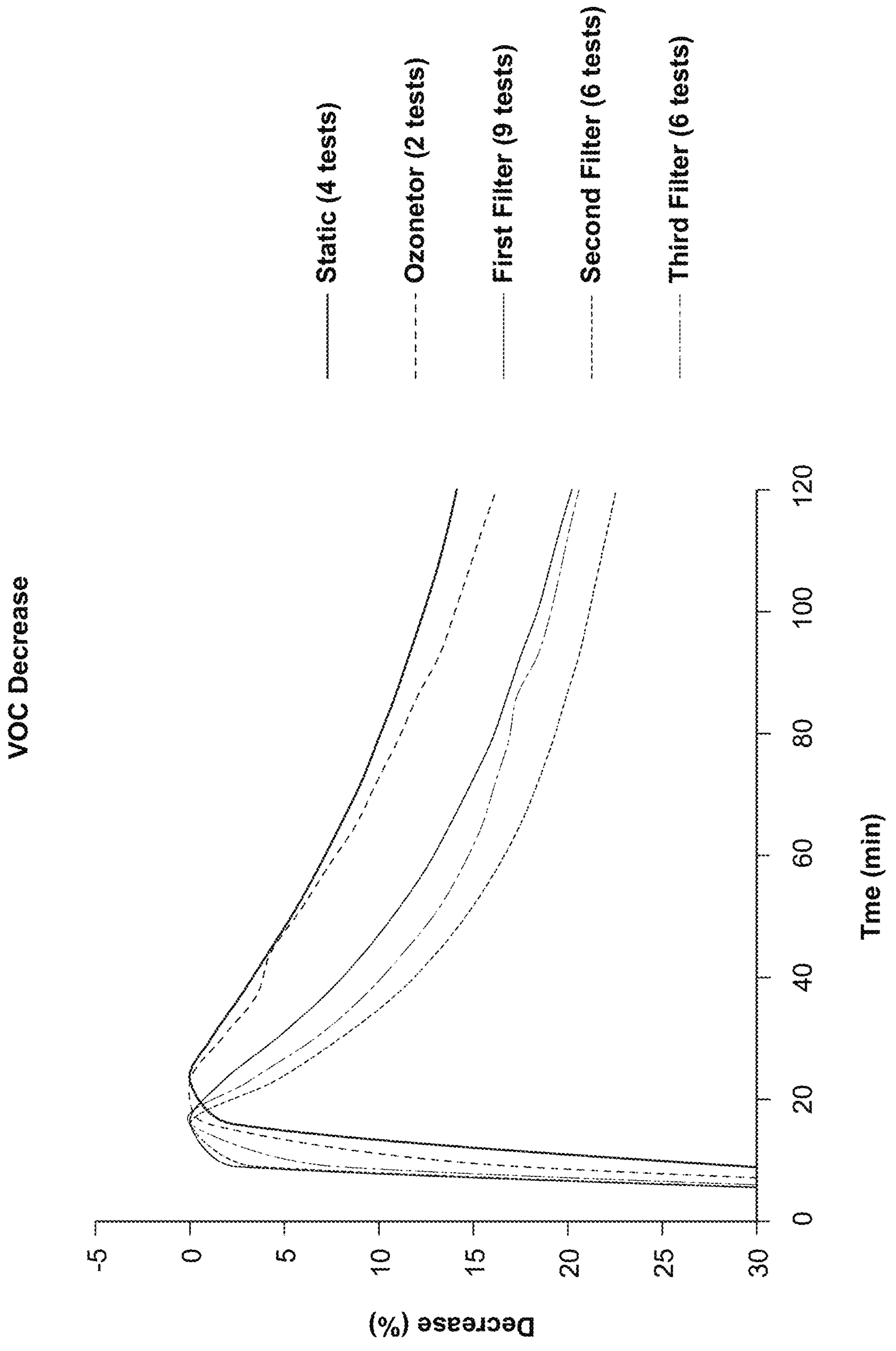
FIG. 11A provides a plot of the percentage of volatile organic compounds over a period of time using different air filters according to some aspects of the present disclosure.
Figure 11B:
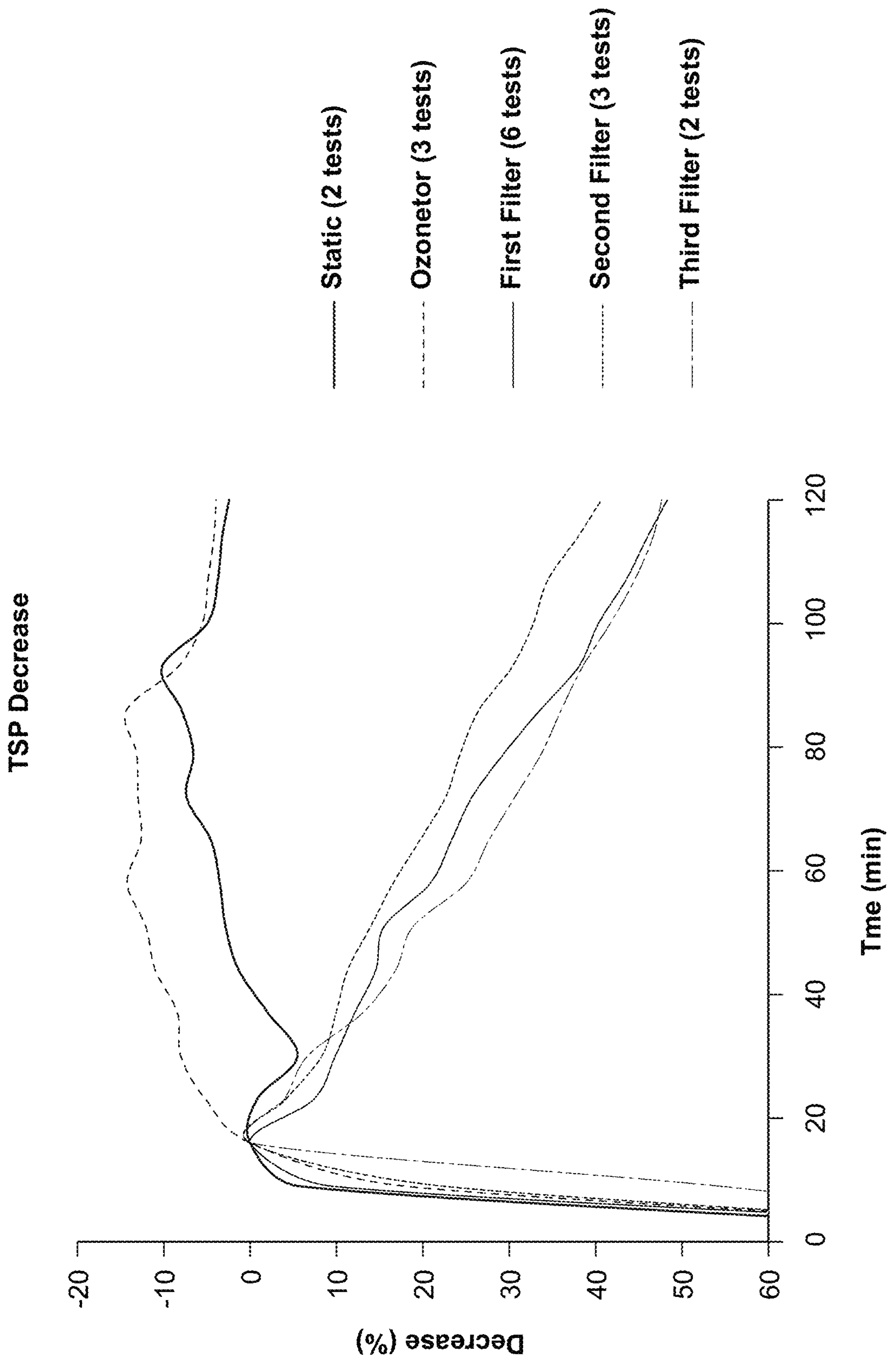
FIG. 11B provides the percentage of total solid particulates over a period of time using different filtration systems according to some aspects of the present disclosure.

Referring now to FIGS. 11A and 11B, a test monitoring the Total Solid Particulate (TSP) and Volatile Organic Compounds (VOC) in a confined environment that is artificially polluted to evaluate the effectiveness of different decontamination devices for household refrigerators is illustrated.

The following five purification and air filtration devices were tested: 1) a Static control environment using no purification and/or air filtration device; 2) Ozonetor; 3) Filter 1, a polymeric filter having no photocatalyst 50 incorporated, 4) Filter 2 activated using UV LEDs, a polymeric filter treated with a first $TiO_2$ doped sol gel as the photocatalyst 50; and 5) Filter 3 activated using UV LEDs, a polymeric filter treated with a second $TiO_2$ doped sol gel as the photocatalyst 50.

Tests were performed in a Glove Box (100 liters per volume) that was polluted by burning about ¼ of a Marlboro cigarette that was able to rapidly generate a large amount of TSP and VOC. The following testing procedure was used: ignition of cigarette, immediate closure of the Glove Box, cigarette combustion, waiting for 15 minutes, switching on the Ozonetor or filter fan, monitoring of up to 120 minutes of TSP content using an Aerocet 531, Met One Instruments, Inc., or monitoring up to 120 minutes of VOC content using a DSIAQ-PLUS-PPC, Gray Wolf Sensing Solutions.

Referring still to FIGS. 11A and 11B, the static control and Ozonetor treatments each were able to reduce the VOC by up to 15% over 120 minutes and had no significant decrease in the TSP during the duration of the experiment. The Filter 1 polymeric filter having no photocatalyst 50 incorporated was able to reduce the VOC by up to about 20% over 120 minutes and the TSP by up to 40% over 120 minutes. The Filter 2 activated with UV LEDs using a polymeric filter treated with a first $TiO_2$ doped sol gel as the photocatalyst 50 was able to reduce the VOC by up to about 20% over 120 minutes and the TSP by up to 50% over 120 minutes. The Filter 3 activated with UV LEDs using a polymeric filter treated with a first $TiO_2$ doped sol gel as the photocatalyst 50 was able to reduce the VOC by up to about 20% over 120 minutes and the TSP by up to 50% over 120 minutes.

In some aspects, the activated filter 50 coupled to the photocatalyst 54 (e.g. $TiO_2$) that is activated using UV LEDs 58 may be able to reduce the VOCs in the storage compartment 22 of the refrigerator 10 by up to about 10%, about 15%, about 20%, or about 25% in 40 minutes, 60 minutes, 80 minutes, 100 minutes, or 120 minutes or less. In some aspects, the activated filter 50 coupled to the photocatalyst 54 (e.g. $TiO_2$) that is activated using UV LEDs 58 may be able to reduce the TSP in the storage compartment 22 of the refrigerator 10 by up to about 10%, about 15%, about 20%, about 25%, about 30%, about 35%, about 40%, or about 45%, in 40 minutes, 60 minutes, 80 minutes, 100 minutes, or 120 minutes or less.

It will be understood by one having ordinary skill in the art that construction of the described device and other components may not be limited to any specific material. Other exemplary aspects of the device disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It will be understood that any described processes or steps within described processes may be combined with other disclosed processes or steps to form structures within the scope of the present device. The exemplary structures and processes disclosed herein are for illustrative purposes and are not to be construed as limiting.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It is also to be understood that variations and modifications can be made on the aforementioned structure without departing from the concepts of the present invention, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

What is claimed is:

1. A refrigerator comprising:

a rear assembly panel coupled with an assembly cover panel, the assembly cover panel including at least one vent;

at least one circulation fan positioned between the rear assembly panel and the assembly cover panel and proximate the at least one vent;

a filter positioned between the rear assembly panel and the assembly cover panel and coupled to a photocatalyst to form an activated carbon filter;

a light-emitting diode (LED) panel assembly including a plurality of LEDs positioned on the rear assembly panel, the LED panel assembly positioned to project light on the activated carbon filter; and an air circulation path extending through the at least one vent and the activated carbon filter, wherein the at least one circulation fan is configured to direct air along the air circulation path, and the activated carbon filter is configured to filter airborne bacteria and particulate matter from the air as the air passes through the activated carbon filter.

2. The refrigerator according to claim 1, wherein the plurality of LEDs project at least one of visible light, UV-A light, UV-B light, and UV-C light.

3. The refrigerator according to claim 1, wherein the activated carbon filter is coupled to a titanium oxide ($TiO_2$) doped sol gel film.

4. The refrigerator according to claim 1, wherein the activated carbon filter is a polymeric filter coupled to a UV activated photocatalyst.

5. The refrigerator according to claim 1, wherein the assembly cover panel includes first and second distal portions positioned on opposing sides of a central portion, wherein the first and second distal portions each include a distal vent and the central portion includes a central vent.

6. The refrigerator according to claim 1, wherein the at least one circulation fan is configured to direct the air circulation path in through the at least one circulation fan and out through the activated carbon filter.

7. The refrigerator according to claim 1, wherein the at least one circulation fan is configured to direct the air circulation path in through the activated carbon filter and out through the at least one circulation fan.

8. The refrigerator according to claim 1, wherein the LED panel assembly includes a first LED panel with white light LEDs and a second LED panel with ultraviolet (UV) LEDs.

9. The refrigerator according to claim 1, wherein the airborne bacteria and the particulate matter are reduced by at least 60% within one minute.

10. A refrigerator, comprising:

a rear assembly panel coupled with an assembly cover panel, the assembly cover panel including first and second distal portions positioned on opposing sides of a central portion, wherein the first and second distal portions each include at least one intake and the central portion includes at least one exhaust;

an ultraviolet (UV) light activated photocatalyst coupled to at least one filter forming an activated filter;

a light-emitting diode (LED) panel assembly having a plurality of LEDs positioned on the rear assembly panel; and an air circulation path defined by the rear assembly panel and the assembly cover panel and extending from the at least one intake, through the activated filter, and out through the at least one exhaust, wherein the activated filter is configured to filter airborne bacteria and particulate matter from air as the air passes through the activated filter and out through the at least one exhaust to circulate filtered air.

11. The refrigerator according to claim 10, wherein the UV light activated photocatalyst is titanium dioxide ($TiO_2$).

12. The refrigerator according to claim 10, wherein the plurality of LEDs project visible light, UV-A light, UV-B light, UV-C light, or a combination thereof onto the UV light activated photocatalyst.

13. The refrigerator according to claim 10, further comprising:

at least two fan assemblies proximate the activated filter.

14. The refrigerator according to claim 10, wherein the central portion of the assembly cover panel includes at least one circulation fan.

15. The refrigerator according to claim 14, wherein the at least one circulation fan includes two, three, or four circulation fans.

16. The refrigerator according to claim 10, wherein at least one of the airborne bacteria and the particulate matter is reduced by at least 60% within ten minutes.

17. An antibacterial fan assembly comprising:

a rear assembly panel coupled with an interior wall of an appliance;

an assembly cover panel coupled with the rear assembly panel to form a housing, wherein the assembly cover panel includes a central portion extending between first and second distal portions, and further wherein the first and second distal portions of the assembly cover panel each include an air intake and the central portion of the assembly cover panel includes an air exhaust;

at least one circulation fan positioned between the rear assembly panel and assembly cover panel, wherein each of the circulation fans is aligned with a corresponding one of the air intakes;

an activated filter positioned proximate, and in circulation with, the air exhaust and having a photocatalyst and an activated carbon, wherein the photocatalyst is a titanium oxide ($TiO_2$) doped sol gel film; and at least one light-emitting diode (LED) positioned to project light on the activated filter.

18. The antibacterial fan assembly of claim 17, wherein the LEDs are positioned to illuminate the activated filter using an ultraviolet (UV) wavelength from about 280 nm to about 405 nm.

19. The antibacterial fan assembly of claim 17, wherein a plurality of LEDs are positioned to project light on the photocatalyst.

20. The refrigerator according to claim 17, wherein the at least one LED includes white light LEDs and UV LEDs.

* * * * *